(12) United States Patent
Shiki et al.

(10) Patent No.: US 10,722,217 B2
(45) Date of Patent: Jul. 28, 2020

(54) ULTRASONIC DIAGNOSTIC APPARATUS AND MEDICAL IMAGE PROCESSING APPARATUS

(71) Applicant: TOSHIBA MEDICAL SYSTEMS CORPORATION, Otawara-Shi (JP)

(72) Inventors: Eiichi Shiki, Otawara (JP); Yoshitaka Mine, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 373 days.

(21) Appl. No.: 15/592,235

(22) Filed: May 11, 2017

(65) Prior Publication Data
US 2017/0340311 A1 Nov. 30, 2017

(30) Foreign Application Priority Data

May 26, 2016 (JP) ................................. 2016-105401
Apr. 21, 2017 (JP) ................................. 2017-084445

(51) Int. Cl.
*A61B 8/08* (2006.01)
*A61B 8/00* (2006.01)

(52) U.S. Cl.
CPC .......... *A61B 8/5207* (2013.01); *A61B 8/4263* (2013.01); *A61B 8/469* (2013.01); *A61B 8/483* (2013.01); *A61B 8/5253* (2013.01); *A61B 8/461* (2013.01)

(58) Field of Classification Search
CPC ....... A61B 8/08; A61B 8/5207; A61B 8/5253; A61B 8/4263; A61B 8/469; A61B 8/483; A61B 8/461

USPC .................................................. 600/433, 407
See application file for complete search history.

(56) References Cited

U.S. PATENT DOCUMENTS

| | | | | |
|---|---|---|---|---|
| 5,540,229 A | * | 7/1996 | Collet-Billon | A61B 8/00 600/443 |
| 6,059,727 A | * | 5/2000 | Fowlkes | A61B 8/08 128/916 |
| 6,315,724 B1 | * | 11/2001 | Berman | A61B 8/0833 128/916 |
| 6,338,716 B1 | * | 1/2002 | Hossack | A61B 8/0833 600/459 |
| 6,554,771 B1 | * | 4/2003 | Buil | A61B 8/00 600/459 |

(Continued)

FOREIGN PATENT DOCUMENTS

| JP | 8-332187 | 12/1996 |
|---|---|---|
| JP | 2006-51360 | 2/2006 |

*Primary Examiner* — Oommen Jacob
(74) *Attorney, Agent, or Firm* — Oblon, McClelland, Maier & Neustadt, L.L.P.

(57) ABSTRACT

An ultrasonic diagnostic apparatus according to a present embodiment includes: a transmitting and receiving circuit configured to transmit an ultrasonic wave to an ultrasonic probe and receive a signal based on the ultrasonic wave received by the ultrasonic probe; a generation circuit configured to generate multiple 2D image data in a chronological order based on the signal; an acquisition circuit configured to acquire three-dimensional multiple position data of the ultrasonic probe; an associating circuit configured to associate the multiple position data with the respective multiple 2D image data; and a correction circuit configured to correct the multiple position data associated by the associating circuit.

23 Claims, 20 Drawing Sheets

(56) References Cited

U.S. PATENT DOCUMENTS

| | | | |
|---|---|---|---|
| 2006/0058651 A1 | 3/2006 | Chiao et al. | |
| 2008/0077001 A1* | 3/2008 | Ruscio | G16H 30/40 |
| | | | 600/407 |
| 2009/0306509 A1* | 12/2009 | Pedersen | G01S 15/8936 |
| | | | 600/446 |
| 2010/0056918 A1* | 3/2010 | Sato | A61B 8/06 |
| | | | 600/443 |
| 2010/0081935 A1* | 4/2010 | Matsumura | A61B 5/6843 |
| | | | 600/443 |
| 2010/0130860 A1* | 5/2010 | Yamagata | A61B 8/13 |
| | | | 600/443 |
| 2011/0087094 A1* | 4/2011 | Ohuchi | A61B 8/08 |
| | | | 600/437 |
| 2017/0340311 A1* | 11/2017 | Shiki | A61B 8/5207 |
| 2018/0153504 A1* | 6/2018 | Herickhoff | A61B 8/085 |
| 2019/0201109 A1* | 7/2019 | Berlinger | G06T 7/248 |

* cited by examiner

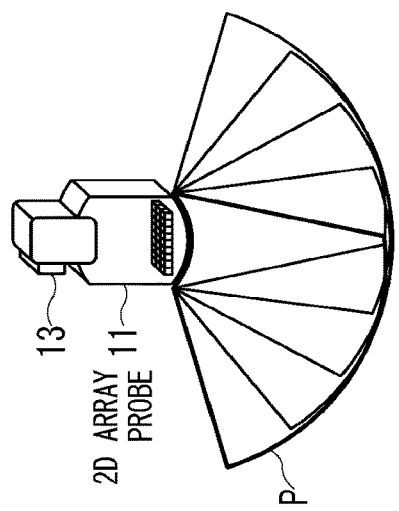
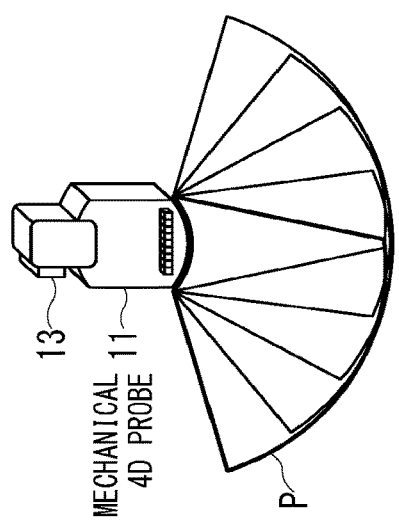
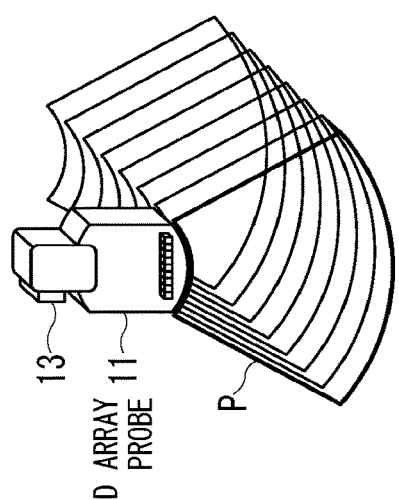
FIG. 2C
FIG. 2B
FIG. 2A

ULTRASONIC DIAGNOSTIC APPARATUS AND MEDICAL IMAGE PROCESSING APPARATUS

CROSS-REFERENCE TO RELATED APPLICATION

This application is based upon and claims the benefit of priority from Japanese Patent Application No. 2016-105401, filed on May 26, 2016, and Japanese Patent Application No. 2017-084445, filed on Apr. 21, 2017, the entire contents of each of which are incorporated herein by reference.

FIELD

An embodiment as an aspect of the present invention relates to an ultrasonic diagnostic apparatus and a medical image processing apparatus.

BACKGROUND

In the medical field, an ultrasonic diagnostic apparatus is used for imaging the inside of a subject using ultrasonic waves generated by multiple transducers (piezoelectric transducers) of an ultrasonic probe. The ultrasonic diagnostic apparatus causes the ultrasonic probe, which is connected to the ultrasonic diagnostic apparatus, to transmit ultrasonic waves into the subject, generates a received signal based on a reflected wave, and obtains a desired ultrasonic image by image processing.

An operator may acquire multiple 2D image data in a chronological order while moving the ultrasonic probe, and may also acquire multiple position data of the ultrasonic probe. In this case, the ultrasonic diagnostic apparatus arranges the multiple 2D image data based on the respective multiple position data and three-dimensionally reconstructs the image data, to thereby generate and display 3D image data.

A problem to be solved by the invention is to provide an ultrasonic diagnostic apparatus and a medical image processing apparatus which are capable of appropriately correcting the multiple position data of the multiple 2D image data.

BRIEF DESCRIPTION OF THE DRAWINGS

In accompanying drawings,

FIGS. 2A to 2C are diagram for explaining scan planes of an ultrasonic probe;

DETAILED DESCRIPTION

An ultrasonic diagnostic apparatus and a medical image processing apparatus according to a present embodiment will be described with reference to the accompanying drawings.

The ultrasonic diagnostic apparatus according to the present embodiment includes: a transmitting and receiving circuit configured to transmit an ultrasonic wave to an ultrasonic probe and receive a signal based on the ultrasonic wave received by the ultrasonic probe; a generation circuit configured to generate multiple 2D image data in a chronological order based on the signal; an acquisition circuit configured to acquire three-dimensional multiple position data of the ultrasonic probe; an associating circuit configured to associate the multiple position data with the respective multiple 2D image data; and a correction circuit configured to correct the multiple position data associated by the associating circuit.

1. ULTRASONIC DIAGNOSTIC APPARATUS ACCORDING TO FIRST EMBODIMENT

Figure 1:
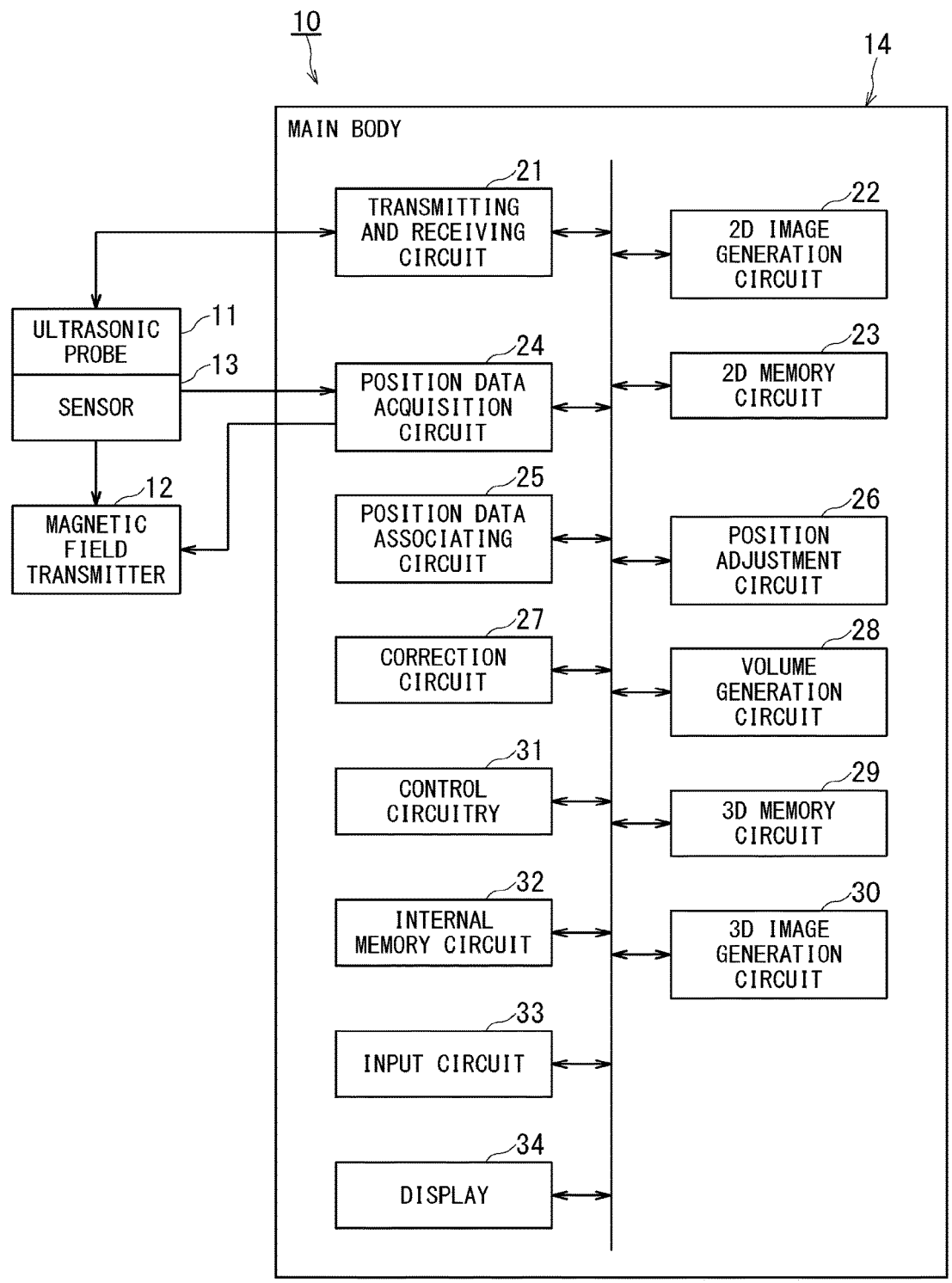
FIG. 1 is a schematic diagram showing a configuration of an ultrasonic diagnostic apparatus according to a first embodiment.

FIG. 1 is a schematic diagram showing a configuration of an ultrasonic diagnostic apparatus according to a first embodiment.

FIG. 1 shows an ultrasonic diagnostic apparatus 10 according to the first embodiment. The ultrasonic diagnostic apparatus 10 includes an ultrasonic probe 11, a magnetic field transmitter 12, a sensor 13, and a main body 14. Note that only the main body 14 may be referred to as the ultrasonic diagnostic apparatus. In this case, the ultrasonic diagnostic apparatus is connected to the ultrasonic probe, the magnetic field transmitter, and the sensor which are provided outside of the ultrasonic diagnostic apparatus.

The ultrasonic probe 11 transmits an ultrasonic wave to a subject (for example, a patient) or receives an ultrasonic wave from the subject. The ultrasonic probe 11 brings the front surface thereof into contact with the surface of the subject to transmit an ultrasonic wave to the subject or receive an ultrasonic wave from the subject. The ultrasonic probe 11 includes small transducers (piezoelectric elements) that are one-dimensionally (1D) or two-dimensionally (2D) arranged at a tip end of the ultrasonic probe. Each of the transducers is an electroacoustic conversion element and has a function of converting an electric pulse into an ultrasonic pulse during transmission and converting a reflected wave into an electric signal (received signal) during reception.

The ultrasonic probe 11 is formed to have a small size and a light weight, and is connected to the main body 14 through a cable. Examples of the type of the ultrasonic probe 11 include a 1D array probe, a mechanical 4D probe, and a 2D array probe. The 1D array probe has a configuration in which transducers are one-dimensionally arranged. In this case, the 1D array probe also includes a configuration in which a small number of transducers are arranged in an elevation direction. The mechanical 4D probe has a configuration in which an array mechanically oscillates in the elevation direction, that is, a direction intersecting a scan plane, the array including multiple transducers one-dimensionally arranged. The 2D array probe has a configuration in which multiple transducers are two-dimensionally arranged.

FIGS. 2A to 2C are diagram for explaining scan planes of the ultrasonic probe 11.

FIG. 2A shows a movement of a scan plane P when the operator manipulates and moves the 1D array probe as the ultrasonic probe 11. In this case, the positions of the sensor 13 and the scan plane P are both fixed with respect to the 1D array probe 11. Accordingly, the conversion of a geometric positional relationship from the sensor 13 to the scan plane P makes it possible to obtain position data of the scan plane P from the position data of the sensor 13. The operator moves the 1D array probe 11 in a direction intersecting with the scan plane P, thereby performing a so-called three-dimensional scanning. Examples of the movement of the 1D array probe 11 include a parallel movement, tilting, and rotation, and the same applies in the following description.

FIG. 2B shows a case where a mechanical 4D probe is caused to move on the scan plane P as the ultrasonic probe 11, and FIG. 2C shows a case where a 2D array probe is caused to move on the scan plane P as the ultrasonic probe 11. FIGS. 2B and 2C show a normal usage of the mechanical 4D probe 11 and the 2D array probe 11, i.e., a case where a tilt angle of a scan plane is automatically set.

As shown in FIG. 2B, in the mechanical 4D probe 11, the 1D array is caused to repeatedly perform scanning in the scan plane P and the 1D array is caused to mechanically oscillate, i.e., perform 3D scanning, in a direction intersecting with the scan plane P.

As shown in FIG. 2C, the 2D array probe 11 moves electrons of an ultrasonic beam in the direction intersecting with the scan plane P, while performing scanning in the scan plane P, thereby performing so-called 3D scanning.

In the cases shown in FIGS. 2B and 2C, the position of the sensor 13 is fixed with respect to the ultrasonic probe 11, and a tilt angle of the scan plane P changes with a lapse of time. The tilt angle of each scan plane P with respect to the ultrasonic probe 11 can be obtained by a calculation, and the geometric positional relationship between the scan planes P can be converted from the position data about the ultrasonic probe 11 and the tilt angle. Therefore, even when a mechanical 4D probe or a 2D array probe is employed as the ultrasonic probe 11, if the scan plane P is fixed to one tilt angle, functions similar to those of the 1D array probe can be achieved.

The mechanical 4D probe or 2D array probe used as the ultrasonic probe 11 can also perform 3D scanning in a manner similar to that when the operator operates the 1D array probe to move. In this case, the operator operates the mechanical 3D probe 11 or the like for repeatedly performing scanning in the scan plane P to move in the state where the scan plane P is fixed to one tilt angle.

As described above, the ultrasonic probe 11 can be treated similarly in any case, regardless of the type of the ultrasonic probe 11. Hereinafter, a case is described in which the 1D array probe repeatedly performs scanning in one scan plane P and the operator manually moves the 1D array probe 11 to perform 3D scanning.

Referring again to FIG. 1, the magnetic field transmitter 12 is disposed in the vicinity of the ultrasonic probe 11 so that the sensor 13 fits inside an effective range of a magnetic field generated from the magnetic field transmitter 12. The magnetic field transmitter 12 generates the magnetic field by the control of the main body 14.

The sensor 13 detects multiple position data of the ultrasonic probe 11 in a chronological order and outputs the multiple position data to the main body 14. The sensor 13 is divided into two types, i.e., a sensor that is attached to the ultrasonic probe 11 and a sensor that is provided separately from the ultrasonic probe 11. The latter type is an optical sensor which photographs feature points of the ultrasonic probe 11 to be measured from multiple positions, and detects each position of the ultrasonic probe 11 according to the principle of triangulation. A case where the former type is used as the sensor 13 will be described below.

The sensor 13 is attached to the ultrasonic probe 11, detects the position data of the sensor 13 itself, and outputs the detected position data to the main body 14. The position data of the sensor 13 can also be regarded as position data of the ultrasonic probe 11. The position data of the ultrasonic probe 11 includes a position and a posture (inclination) of the ultrasonic probe 11. For example, the magnetic field transmitter 12 sequentially transmits triaxial magnetic fields and the sensor 13 sequentially receives the magnetic fields, thereby making it possible to detect the posture of the ultrasonic probe 11. The sensor 13 may be a so-called 9-axis sensor including at least one of a triaxial gyroscopic sensor for detecting a triaxial angular velocity in a three-dimensional space, a triaxial acceleration sensor for detecting a triaxial acceleration in a three-dimensional space, and a triaxial geomagnetic sensor for detecting a triaxial terrestrial magnetism in a three-dimensional space.

The main body 14 includes a transmitting and receiving circuit 21, a 2D image generation circuit 22, a 2D memory circuit 23, a position data acquisition circuit 24, a position data associating circuit 25, a position adjustment circuit 26, a correction circuit 27, a volume generation circuit 28, a 3D memory circuit 29, a 3D image generation circuit 30, control circuitry 31, an internal memory circuit 32, an input circuit 33, and a display 34. The transmitting and receiving circuit 21, the 2D image generation circuit 22, the position data acquisition circuit 24, the position data associating circuit 25, the position adjustment circuit 26, the correction circuit 27, the volume generation circuit 28, and the 3D image generation circuit 30 are composed of a field programmable gate array (FPGA) or the like.

The transmitting and receiving circuit 21 transmits an ultrasonic wave to the ultrasonic probe 11 according to a control signal from the control circuitry 31, and receives a signal (received signal) based on the ultrasonic wave received by the ultrasonic probe. The transmitting and receiving circuit 21 includes a transmission circuit which generates a drive signal for causing the ultrasonic probe 11 to radiate a transmitter pulse, and a reception circuit which performs phasing addition on the received signal from the ultrasonic probe 11.

The transmission circuit includes a rate pulse generator, a transmission delay circuit, and a pulser. The rate pulse generator generates a rate pulse for determining a repetition cycle of a transmitter pulse by dividing a continuous wave or a rectangular wave supplied from a reference signal generation circuit, and supplies the rate pulse to the transmission delay circuit. The transmission delay circuit is composed of a number of independent delay circuits corresponding to the number of transducers used for transmission. The transmission delay circuit provides the rate pulse with a delay time for focusing the transmitter pulse at a predetermined depth so as to obtain a fine beam width in the transmission, and with a delay time for radiating the transmitter pulse in a predetermined direction, and supplies the rate pulse to the pulser. The pulser includes an independent drive circuit and generates a drive pulse for driving the transducers incorporated in the ultrasonic probe 11 based on the rate pulse.

The reception circuit of the transmitting and receiving circuit 21 includes a pre-amplifier, an analog-to-digital (A/D) conversion circuit, a reception delay circuit, and an addition circuit. The pre-amplifier secures a sufficient S/N by amplifying small signals converted into electric received signals by the transducers. The received signal amplified to a predetermined size by the pre-amplifier is converted into a digital signal by the A/D conversion circuit and is transmitted to the reception delay circuit. The reception delay circuit provides the received signal output from the A/D conversion circuit with a convergence delay time for focusing a reflected wave from the predetermined depth and with a deflection delay time for setting a reception directivity in the predetermined direction. The addition circuit performs phasing addition (addition by matching the phases of received signals obtained in the predetermined direction) on the received signals from the reception delay circuit.

The 2D image generation circuit 22 generates multiple 2D image data in a chronological order, i.e., 2D image data in multiple frames, based on the received signals received from the reception circuit of the transmitting and receiving circuit 21 according to the control signal from the control circuitry 31. Examples of the type of the multiple 2D image data include B-mode image data, color mode image data, and application mode image data such as electrography.

In general, a color mode image and an application mode image are displayed in a superimposed manner on a B-mode image as a background image. Accordingly, even in the mode for generating these images, B-mode image data is generated. A data region for the color mode image data and the application mode image data is restricted, and thus the data is not suitable for the position adjustment processing performed by the position adjustment circuit 26 to be described later. Accordingly, even when in the mode for generating these images, it is preferable to perform position adjustment processing using the B-mode image data.

Examples of the form of the multiple 2D image data include raw data composed of multiple raster data in the scan plane P (shown in FIGS. 2A to 2C) corresponding to a certain time phase, and SC data obtained by performing scan conversion (SC) processing on raw data. In what follows, the case that the 2D image data is the low data is explained unless otherwise stated.

The 2D memory circuit 23 is a memory circuit including multiple memory cells that correspond to multiple frames and are formed in two axial directions for each frame. The 2D memory circuit 23 stores the multiple raw data, generated by the 2D image generation circuit 22, in a chronological order. Since the ultrasonic probe 11 is manipulated and moved by the operator, the multiple raw data arranged in a chronological order are data located at multiple positions. Time data associated with the acquisition for raster data is attached to raster data, included in each piece of the multiple raw data, by a system timer.

The position data acquisition circuit 24 controls the magnetic field transmitter 12 to cause the magnetic field transmitter 12 to transmit a magnetic field, and acquires multiple position data of the ultrasonic probe 11 from the sensor 13, in a chronological order. The position data acquisition circuit 24 acquires the multiple position data, each piece of the multiple position data corresponding to the raw data, i.e., to the scan plane for the multiple raw data. The position data of the scan plane includes the position and the posture of the scan plane.

It is possible for the position data acquisition circuit 24 to convert the multiple position data of the sensor 13 into the multiple position data of the scan planes for the multiple raw data, based on the geometric positional relationship to each point of the scan plane for the raw data. When a mechanical 4D probe (shown in FIG. 2B) is used as the ultrasonic probe 11, position data about the scan plane is obtained based on the position data about the sensor 13 and the tilt angle (angle of oscillation) of the scan plane. When the 2D array probe (shown in FIG. 2C) is used as the ultrasonic probe 11, position data about the scan plane is obtained based on the position data about the sensor 13 and the tilt angle (angle of ultrasonic beam) of the scan plane.

The position data associating circuit 25 associates the multiple position data acquired by the position data acquisition circuit 24 with the respective multiple raw data generated by the 2D image generation circuit 22. The position data associating circuit 25 compares time data, attached to each piece of the multiple raw data, with time data, attached to each of the multiple position data, and associates position data, having a time that is closest to, immediately before, or immediately after a time of each piece of the multiple raw data, with the raw data. In this case, the time of each piece of the multiple raw data may be a time attached to the first piece of the raster data among the multiple raster data comprising the each piece of the multiple raw data, a time attached to the center raster data, or an average time of the multiple raster data.

The method for matching the time of the multiple raw data with the time of the multiple position data is not limited to the above method. For example, the position data may be associated with the corresponding piece of multiple raw data by synchronizing the acquisition for position data by the sensor 13 and the position data acquisition circuit 24 with the acquisition for raw data.

The position data associating circuit 25 can attach the multiple position data to the respective multiple raw data so that the multiple position data are associated with the respective multiple raw data. For example, the position data associating circuit 25 writes the position data into a header, a footer, or the like of each piece of the multiple raw data. The multiple raw data to which the respective multiple position data is attached is stored in the 2D memory circuit 23.

In another alternative, the position data associating circuit 25 may write the raw data and the position data into a correspondence table so that the position data is associated with each piece of the multiple raw data. A case where the position data is attached to each piece of the multiple raw data so that the position data is associated with each piece of the multiple raw data will be described below by way of example.

The position adjustment circuit 26 and the correction circuit 27 function as a "correction unit". The position adjustment circuit 26 and the correction circuit 27 perform spatial position adjustment of multiple raw data in such a manner that the position data associating circuit 25 corrects the position data attached to each of the multiple raw data. The position adjustment circuit 26 performs position adjustment processing on multiple raw data arranged in accordance with the attached position data, and calculates multiple position correction data. A position adjustment processing method will be described later with reference to FIGS. 4A to 6. Further, the correction circuit 27 corrects the position data attached to each of the raw data by using corresponding position correction data calculated by the position adjustment circuit 26, and replaces the position data with corrected position data.

Figure 3:
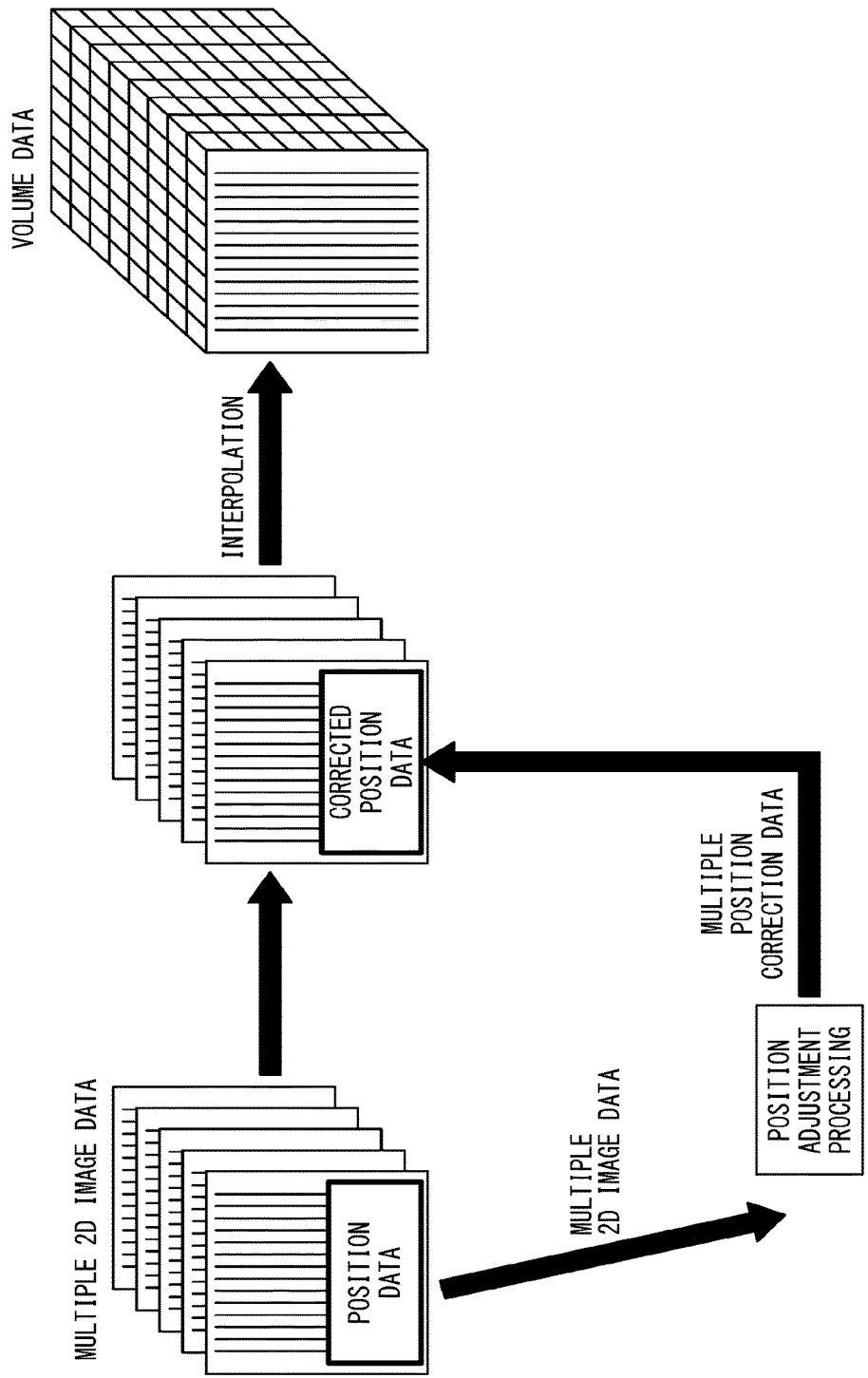
FIG. 3 is a conceptual diagram for explaining an outline of a method for correcting position data attached to 2D image data in the ultrasonic diagnostic apparatus according to the first embodiment.

FIG. 3 is a conceptual diagram for explaining an outline of a method for correcting position data attached to 2D image data in the ultrasonic diagnostic apparatus 10.

As shown on the left side of FIG. 3, position data is attached to each of the 2D image data (raw data or SC data). By performing position adjustment processing on each of the 2D image data arranged in accordance with the attached position data, position correction data for each of the 2D image data is calculated. When the position data attached to each of the 2D image data is corrected using the corresponding position correction data, the position data attached to each of the multiple 2D image data is replaced by the corrected position data.

FIGS. 4A to 6 are diagrams for explaining the position adjustment processing.

To perform the position adjustment, SC data in which an image directly corresponds to a spatial shape of an object is used. However, if a coordinate conversion for position adjustment processing to be described later, as well as a conversion from raw data to SC data can be obtained in a table format, SC data is not necessarily used for position adjustment and instead raw data may be used. Thus, the conversion in a table format is advantageous in terms of processing rate. The following description is made assuming a case where the conversion in a table format is obtained using raw data. However, as mentioned above, since the actual position adjustment is performed using SC data, an SC data format is used in the figures, for ease of understanding.

Figure 4A:
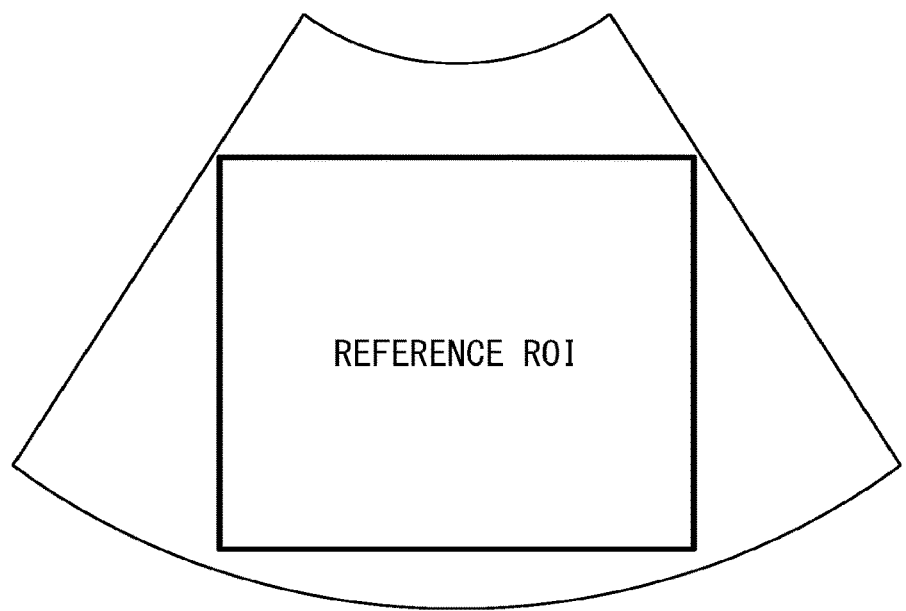
FIGS. 4A and 4B are diagrams for explaining a position adjustment processing.

Raw data corresponding to two frames is selected from the multiple raw data. As shown in FIG. 4A, one ROI (Region of Interest) is set as a reference ROI on one (reference raw data) of the raw data corresponding to two frames. FIG. 4A shows a case where the reference ROI has a rectangular shape. However, the shape of the reference ROI is not limited to this.

Figure 5:
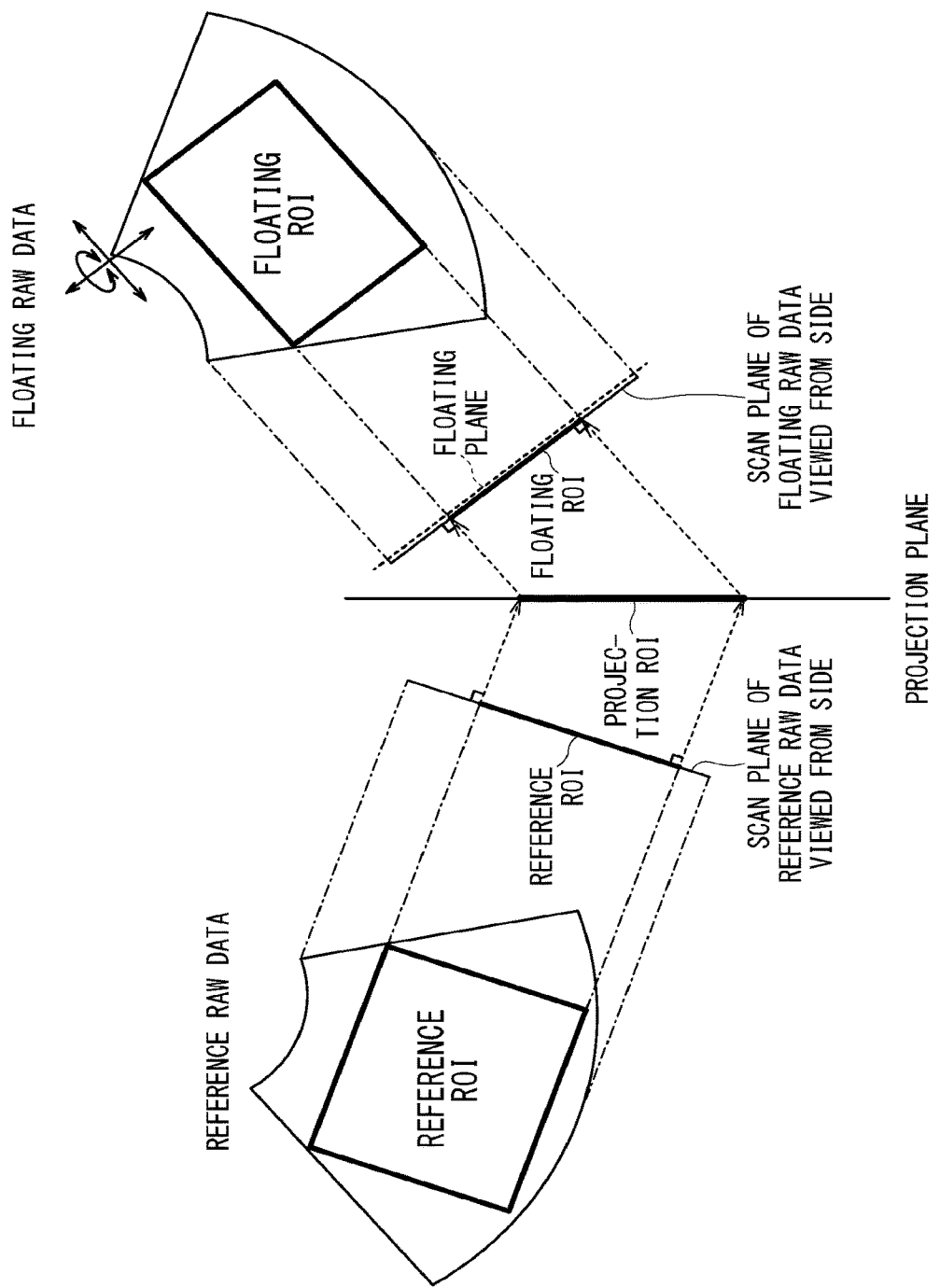
FIG. 5 is a diagram for explaining the position adjustment processing.

As shown in FIG. 5, the scan plane associated with the reference raw data and the scan plane associated with other raw data (floating raw data) are arranged based on the position data attached to each of the raw data. A virtual projection plane is set between the position of the scan plane associated with the reference raw data and the position of the scan plane associated with the floating raw data. Further, a contact of a perpendicular to the reference ROI with the projection plane is set as a projection ROI on the projection plane. Next, a straight line perpendicular to the scan plane associated with the floating raw data is drawn from the projection ROI toward the scan plane, and a contact of the straight line with the scan plane associated with the floating raw data is set as a floating ROI. The floating ROI is present on the floating raw data.

The floating plane whose position and angle match those of the scan plane associated with the floating raw data is set. The floating raw data is moved (parallel or rotation moving) on the floating plane in the state where the floating ROI is fixed to the floating plane, the image in the floating ROI fixed to the floating plane is changed. In other words, the floating raw data is moved on the floating plane in the state where the floating ROI is fixed to the floating plane, and multiple floating raw data parts (shown in FIG. 6) associated with multiple positions in the floating ROI are obtained based on the floating raw data.

Figure 6:
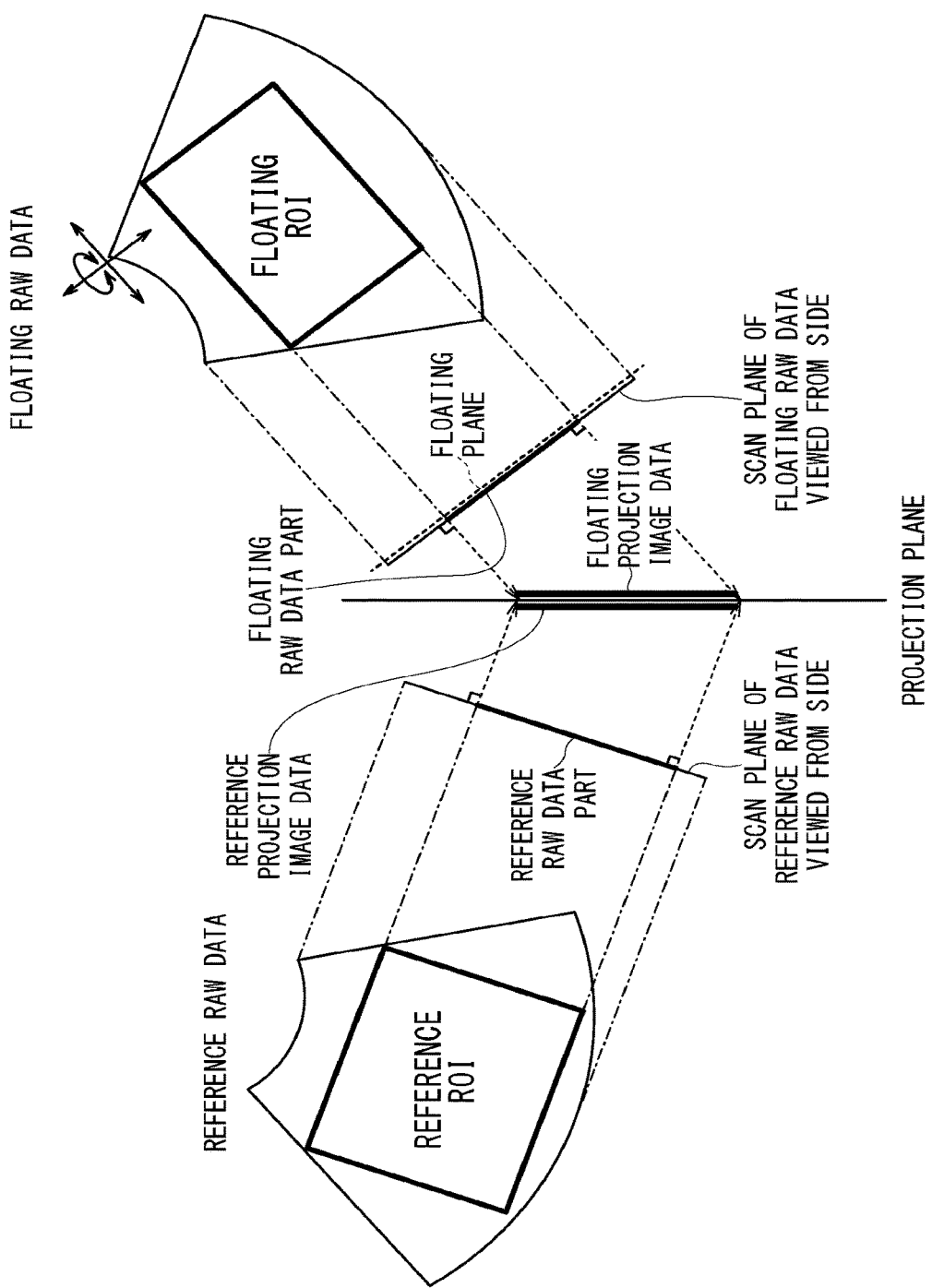
FIG. 6 is a diagram for explaining the position adjustment processing.

As shown in FIG. 6, the reference raw data part in the reference ROI based on the reference raw data is projected onto the projection plane, thereby obtaining reference projection image data. The multiple floating raw data parts in the floating ROI based on the floating raw data are each projected to the projection plane, thereby obtaining multiple floating projection image data. The similarity measure with the reference projection image data is calculated for each of the multiple floating projection image data, and the similarity measures are compared. The floating projection image data obtained when the similarity measure is maximum (value is minimum) is considered to match the reference projection image data. Further, the amount of displacement to the floating raw data associated with the floating projection image data obtained when the similarity measure is maximum is obtained as the position correction data from initial floating raw data obtained before displacement.

In the comparison of the similarity measures, for example, the correlation between both projection image data is used. For example, as shown in the following Formula (1) or (2), there is a method for adding the absolute value of the difference between pixel values of the projection plane is added for all pixels in the projection plane and considering the positions where the additional value is minimum to be matched. In the following Formula (1) or (2), aj represents a pixel value of reference projection image data; bj represents a pixel value of floating projection image data; j represents a pixel in the projection ROI; and N represents the total number of pixels in the projection ROI. In this method, the processing is simple, which is advantageous in processing speed.

$$\min \sum_{i}^{N} \text{abs}(aj - bj) \quad (1)$$

$$\min\left(\frac{1}{N}\right)\sum_{1}^{N} \text{abs}(aj - bj) \quad (2)$$

In this case, it is desirable that the pieces of raw data corresponding to two frames to be selected be temporally or positionally adjacent to each other. The frame rate is several tens Hz, which is a high frame rate, and the time difference between the raw data corresponding to two adjacent frames is small. Accordingly, it can be considered that no large change occurs in the motion between the two frames. For this reason, the displacement of the tilt angle with respect to the floating plane of the floating raw data during position adjustment is already omitted and simplified. When the floating raw data is moved on the floating plane, the rotational displacement may be omitted and simplified, which leads to an improvement in processing time. For the same reason, the positions on the scan plane of the raw data corresponding to two adjacent frames are already substantially matched based on the position data. Accordingly, there is no need to greatly increase the range in which the floating raw data is moved on the floating plane. This configuration requires a relatively short processing time as compared to a case where the position adjustment processing is performed using only raw data, without using the sensor 13. As described above, the position adjustment processing is performed based on the similarity measure between the reference projection image data based on the reference raw data and the floating projection image data based on the floating raw data, thereby calculating the position correction data for the floating raw data. The processing for calculating the position correction data is sequentially performed using the floating raw data for which the position correction data is calculated as the reference raw data and other raw data as floating raw data. Thus, for example, when the operation for causing the ultrasonic probe 11 to move on the object surface is carried out, the position adjustment is sequentially performed and the entire position adjustment is performed. The ROI is set in the raw data, thereby making it possible to perform position adjustment in a living body without being affected by the irregularities of the object surface.

When the interval between frames is narrower than the spatial resolution of the ultrasonic wave, the frames may be thinned out. This leads to a reduction in the entire processing time for the multiple reference raw data. In this case, two adjacent frames indicate two adjacent frames obtained after thinning out the frames.

Figure 4B:
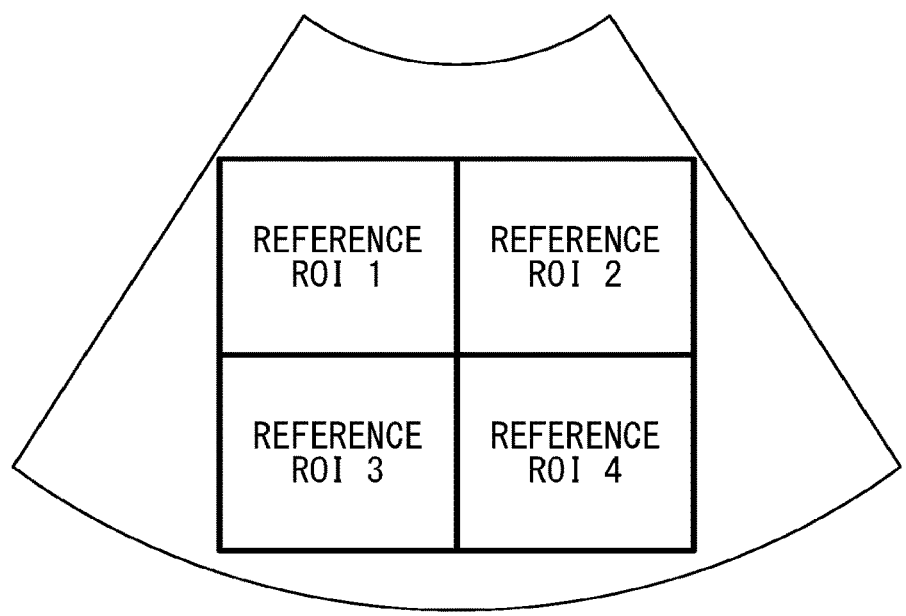

The present invention is not limited to the case where one reference ROI is set on the reference raw data. As shown in FIG. 4B, multiple reference ROIs (reference ROI_1 to reference ROI_4) may be set on the reference raw data. When multiple reference ROIs are set, a position correction data element is obtained for each reference ROI. A representative value of these elements is used as the entire position correction data. To obtain the representative value, various measures for obtaining an appropriate value can be taken. For example, simple calculation of an average value, as well as calculation of an average value by eliminating a value which is apart from another value by a certain value or more, and taking a median.

Referring again to FIG. 1, the correction circuit 27 corrects the position data attached to each of the multiple raw data stored in the 2D memory 23 based on the position correction data obtained by the position adjustment circuit 26, and the position data is replaced by the corrected position data.

The volume generation circuit 28 arranges the multiple raw data, stored in the 2D memory 23, in the 3D memory 29 in accordance with the corrected position data, and performs three-dimensional reconstruction for performing interpolation processing as needed, thereby generating volume data in the 3D memory 29. A well-known technique is used as the interpolation processing method. Examples of the well-known technique include a technique disclosed by Trobaugh, J. W., Trobaugh, D. J., Richard W. D. "Three-Dimensional Imaging with Stereotactic Ultrasonography", Computerized Medical Imaging and Graphics, 18: 5, 315-323, 1994 (hereinafter referred to as "Non-Patent Literature").

In the technique disclosed in Non-Patent Literature, raw data corresponding to adjacent two frames are arranged in a space using position data, and a pixel value on a plane between the data is calculated from the value of a proximal point (pixel) by interpolation such as nearest neighbor, bilinear interpolation, or bicubic interpolation. The volume generation circuit 28 corrects the acquired multiple position data in accordance with the correcting result by the correction circuit 27, and generates volume data, based on multiple raw data arranged according to the corrected multiple position data, using the technique disclosed in Non-Patent Literature.

The 2D image data acquisition, the position data acquisition, the position data attachment, the position adjustment, the position data correction, and the volume data generation may be sequentially performed. In this case, it is preferable to perform a part or whole of the position adjustment, the position data correction, and the volume data generation in parallel with the 2D image data acquisition, the position data acquisition, and the position data attachment. From the above-mentioned processing content, the position adjustment, the position data correction, and the volume data generation can be started from a time when several frames are acquired, even if not all pieces of the 2D image data are obtained. As a result of the parallel processing as described above, the position data correction or the volume data generation is finished at substantially the same time when all pieces of the 2D image data are obtained. Consequently, a waiting time from the end of the data acquisition to the volume data generation is considerably reduced.

The 3D memory circuit 29 is a memory circuit including multiple memory cells in three axial directions (X-axis, Y-axis, and z-axis directions). The 3D memory circuit 29 stores the volume data generated by the volume generation circuit 28. Assuming a case where the ultrasonic probe 11 is moved in parallel in the direction intersecting with the scan plane, a spatial resolution is generally secured by setting the X-axis and the Y-axis as the scan plane and setting the Z-axis as the movement direction. Accordingly, the scan plane of the ultrasonic probe 11 is set so as to extend over the X-axis plane and the Y-axis plane.

The 3D image generation circuit 30 performs 3D image processing, such as MPR (Multi-Planar Reconstruction) processing, volume rendering processing, surface rendering processing, and MIP (Maximum Intensity Projection) processing, on the volume data stored in the 3D memory circuit 29. Further, the 3D image generation circuit 30 performs 3D image processing on the volume data, thereby generating 3D image data such as MPR image data, volume rendering image data, surface rendering image data, and MIP image data. Furthermore, the 3D image generation circuit 30 displays the 3D image data on the display 34 as a 3D image.

Figure 11B:
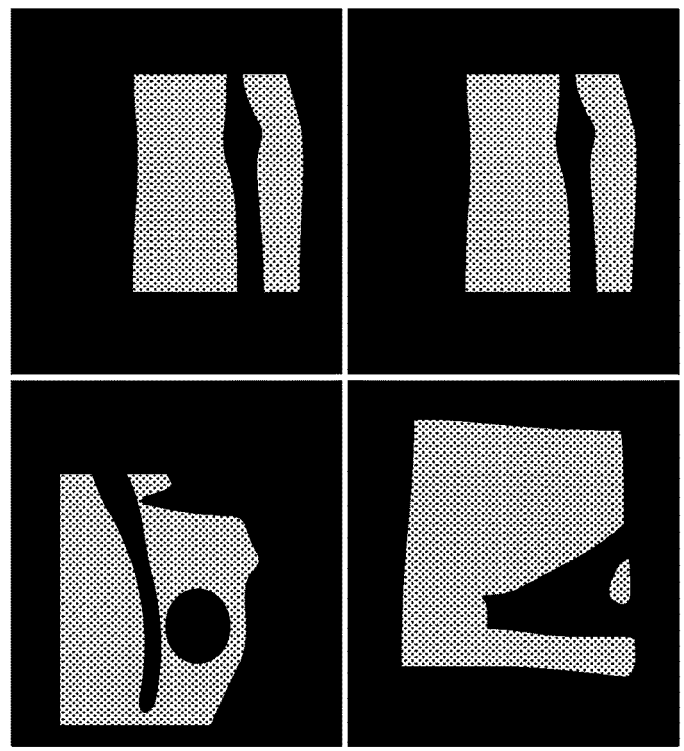
FIG. 11B is a diagram showing a display example of a 3D image by the ultrasonic diagnostic apparatus according to the second embodiment.

The 3D image displayed on the display 34 by the 3D image generation circuit 30 is similar to that shown in FIG. 11B. A distortion in the tissue in 3D image shown in FIG. 11B is considerably improved as compared to the 3D image of the related art shown in FIG. 11A.

The control circuitry 31 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The control circuitry 31 reads out a program, which is stored in the internal memory circuit 32 or is directly incorporated into the control circuitry 31, and executes the program, thereby comprehensively controlling the processing operations of the units 21 to 30 and 32 to 34.

The control circuitry 31 may be a single processing circuit or a combination of multiple processing circuit elements. In the latter case, the internal memory circuit 32 includes multiple memory circuit elements each storing an element of a program that the control circuitry 31 executes, and each corresponding to the processing circuit element. Alternatively, in the latter case, the internal memory circuit 32 includes a single memory circuit storing the program that the control circuitry 31 executes, and corresponding to the processing circuit element.

The internal memory circuit 32 is composed of a semiconductor memory element, such as a RAM (random access memory) or a flash memory, a hard disk, an optical disk, or the like. The internal memory circuit 32 may be composed of a portable medium such as a USB (universal serial bus) memory, or a DVD (digital video disk). The internal memory circuit 32 stores various processing programs (including an application program, as well as an OS (operating system)) used in the control circuitry 31, and data necessary for executing the programs. The OS may include a GUI (graphical user interface) with which basic operations can be performed by the input circuit 33 by making great use of graphics for a display of information for the operator on the display 34.

The input circuit 33 is a circuit which inputs a signal from an input device that is operable by the operator. In this case, the input device itself is included in the input circuit 33. The input device includes a pointing device (such as a mouse), a keyboard, a track ball, and various buttons. When the input device is manipulated by the operator, the input circuit 33 generates an input signal according to the manipulation and outputs the input signal to the control circuitry 31. The main body 14 may include a touch panel having a configuration in which the input device is integrated with the display 34.

The input circuit 33 outputs a transmission condition set by the operator to the control circuitry 31. Examples of the transmission condition include a center frequency of an ultrasonic wave transmitted through the ultrasonic probe 11. The center frequency varies depending on a sweep system (linear, convex, sector, etc.), a region to be diagnosed of a subject, an ultrasonic diagnosis mode (such as B-mode, Doppler mode, and color Doppler mode), a distance from the surface of the subject to the region to be diagnosed, or the like.

The input circuit 33 includes a button that is operable by the operator to start data acquisition, a button for terminating the data acquisition, and a switch for switching whether or not to perform the position adjustment.

The display 34 is includes a general display output device such as a liquid crystal display or an OLED (organic light emitting diode) display. The display 34 displays, as a 3D image, the 3D image data generated by the 3D image generation circuit 30 or the like by the control of the control circuitry 31.

Next, an operation of the ultrasonic diagnostic apparatus 10 will be described with reference to FIGS. 1 and 7.

Figure 7:
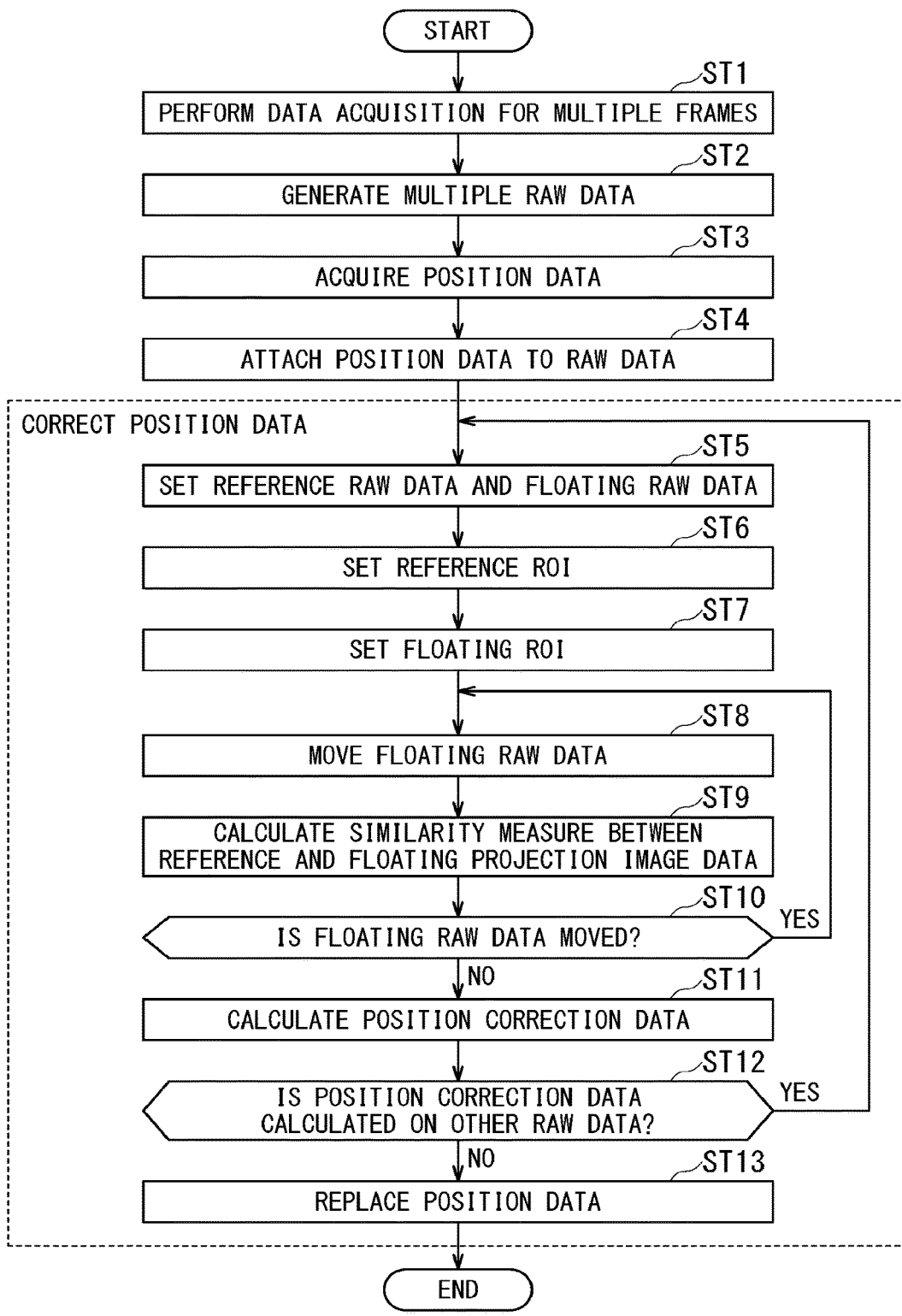
FIG. 7 is a flowchart showing an operation of the ultrasonic diagnostic apparatus according to the first embodiment.

FIG. 7 is a flowchart showing an operation of the ultrasonic diagnostic apparatus 10.

When the button for starting the data acquisition as the input circuit 33 is pressed by the operator, the transmitting and receiving circuit 21 controls the ultrasonic probe 11 to execute ultrasonic waves transmitting and receiving, and performs data acquisition for multiple frames (step ST1). The 2D image generation circuit 22 generates multiple raw data in a chronological order based on the data acquired in step ST1 (step ST2).

The position data acquisition circuit 24 acquires the multiple position data of the ultrasonic probe 11 from the sensor 13, each of the multiple position data corresponding to each piece of the multiple raw data (step ST3). The position data associating circuit 25 attaches the position data acquired in step ST3 to each piece of the multiple raw data generated in step ST2 (step ST4). The multiple raw data to which the position data is attached in step ST4 is stored in the 2D memory circuit 23.

The position adjustment circuit 26 and the correction circuit 27 correct the position data attached to each of the multiple raw data are corrected, thereby matching the spatial positions. Specifically, the position adjustment circuit 26 performs position adjustment processing on the multiple raw data arranged in accordance with the position data attached in step ST4, and calculates the multiple position correction data. The correction circuit 27 corrects the position data attached to each of the raw data by using the corresponding position correction data calculated by the position adjustment circuit 26, and replaces the position data with the corrected position data.

The position adjustment circuit 26 sets the reference raw data and the corresponding floating raw data from the multiple raw data (step ST5). As shown in FIG. 4A, the position adjustment circuit 26 sets the reference ROI on the reference raw data set in step ST5 (step ST6).

As described above with reference to FIG. 5, the position adjustment circuit 26 sets the floating ROI on the scan plane associated with the floating raw data based on the reference ROI of the reference raw data (step ST7). As described above with reference to FIG. 5, the position adjustment circuit 26 moves (parallel displacement and rotational displacement) the floating raw data on the floating plane in the state in which the floating ROI is fixed to the floating plane (step ST8). Thus, multiple floating raw data parts associated with multiple positions in the floating ROI are obtained based on the floating raw data.

As described above with reference to FIG. 6, the position adjustment circuit 26 projects a reference raw data part in the reference ROI based on reference raw data onto the projection plane, thereby obtaining reference projection image data, and the floating raw data part in the floating ROI based on the floating raw data is projected onto the projection plane, thereby obtaining the floating projection image data. As described above with reference to FIG. 6, the position adjustment circuit 26 calculates the similarity measure with the reference projection image data for the floating projection image data (step ST9). The position adjustment circuit 26 determines whether or not to calculate another similarity measure, i.e., whether or not to move the floating raw data on the floating plane (step ST10).

When the determination result in step ST10 indicates YES, i.e., when it is determined that the floating raw data is moved on the floating plane, the position adjustment circuit 26 moves the floating raw data on the floating plane in the state where the floating ROI is fixed to the floating plane (step ST8).

On the other hand, when the determination result in step ST10 indicates NO, i.e., when it is determined that the floating raw data is not moved on the floating plane, the position adjustment circuit 26 compares multiple similarity measures calculated in step ST9, and calculates, as position correction data, the amount of displacement to the position of the floating raw data associated with the floating projection image data obtained when the similarity measure is maximum, from the position of the initial floating raw data obtained before displacement (step ST11).

The position adjustment circuit 26 determines whether or not to calculate the position correction data on other raw data (step ST12). When the determination result in step ST12 indicates YES, i.e., when it is determined that the position correction data is calculated on other raw data, the position adjustment circuit 26 sets the reference raw data and the corresponding floating raw data on other raw data (step ST5).

On the other hand, when the determination result in step ST12 indicates NO, i.e., when it is determined that the position correction data is not calculated on other raw data, or when it is determined that the position correction data is calculated using desired raw data, the correction circuit 27 corrects the position data attached to each of the multiple raw data in step ST4 based on the position correction data calculated in step ST11, and replaces the position data with the corrected position data (step ST13). When the button for starting the data acquisition as the input circuit 33 is pressed by the operator, the data acquisition started in step ST1 is finished at any timing.

The ultrasonic diagnostic apparatus 10 arranges the multiple raw data according to the multiple position data attached to the respective multiple raw data, performs the position adjustment between two raw data, thereby making it possible to appropriately correct the multiple position data.

2. ULTRASONIC DIAGNOSTIC APPARATUS ACCORDING TO SECOND EMBODIMENT

The ultrasonic diagnostic apparatus according to the second embodiment performs image processing appropriately on multiple raw data to be subjected to position adjustment so as to improve the accuracy of the position adjustment, in addition to obtaining the advantageous effects provided by the ultrasonic diagnostic apparatus 10 described above.

Figure 8:
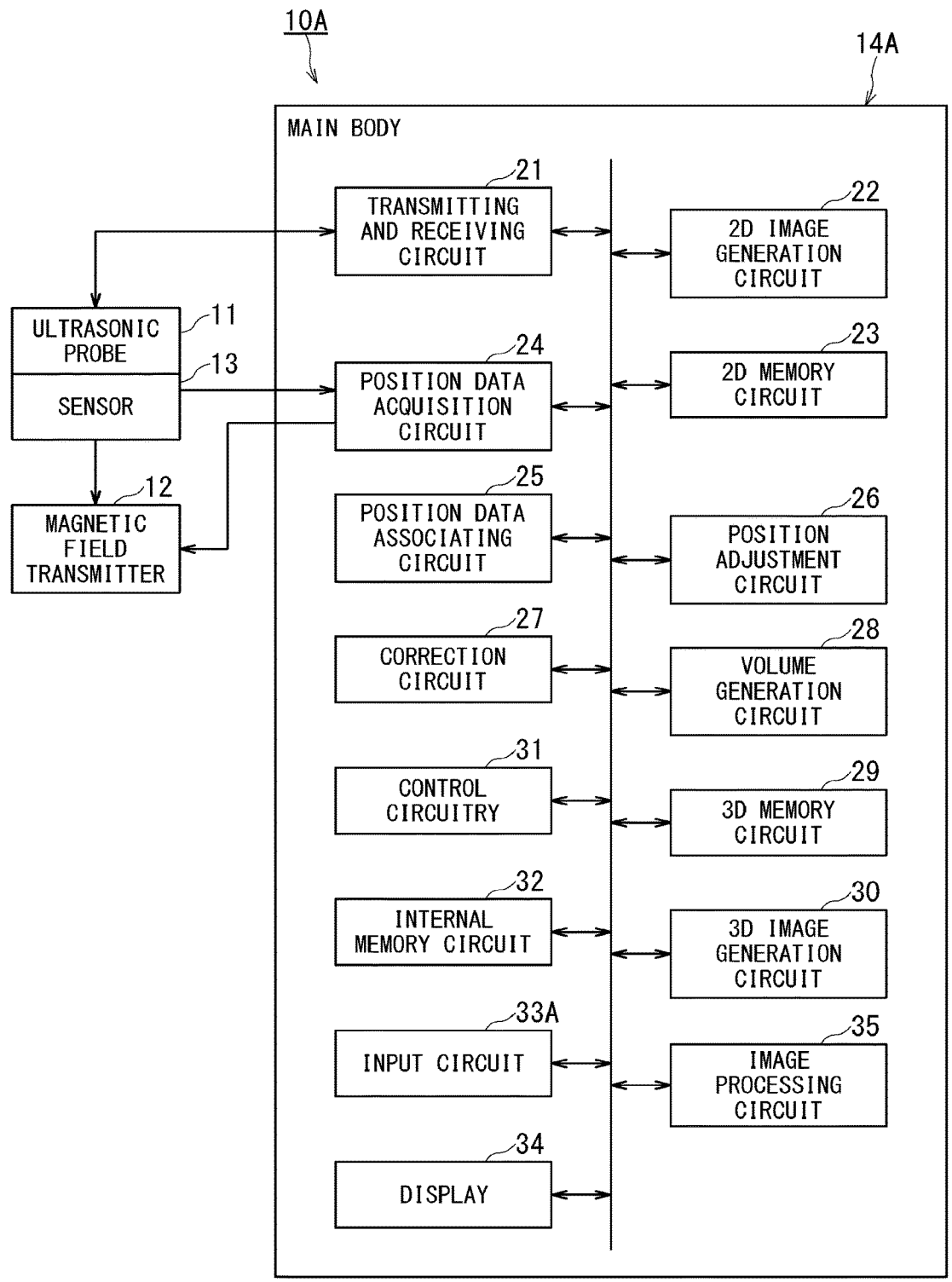
FIG. 8 is a schematic diagram showing a configuration of an ultrasonic diagnostic apparatus according to a second embodiment.

FIG. 8 is a schematic diagram showing a configuration of an ultrasonic diagnostic apparatus according to a second embodiment.

FIG. 8 shows an ultrasonic diagnostic apparatus 10A according to the second embodiment. The ultrasonic diagnostic apparatus 10A includes the ultrasonic probe 11, the magnetic field transmitter 12, the sensor 13, and a main body 14A. Note that only the main body 14A may be referred to as the ultrasonic diagnostic apparatus. In this case, the ultrasonic diagnostic apparatus is connected to the ultrasonic probe, the magnetic field transmitter, and the sensor which are provided outside of the ultrasonic diagnostic apparatus.

In FIG. 8, the same symbols are assigned to the same components as those in the ultrasonic diagnostic apparatus 10 shown in FIG. 1. The description of these components is omitted.

The main body 14A includes the transmitting and receiving circuit 21, the 2D image generation circuit 22, the 2D memory circuit 23, the position data acquisition circuit 24, the position data associating circuit 25, the position adjustment circuit 26, the correction circuit 27, the volume generation circuit 28, the 3D memory circuit 29, the 3D image generation circuit 30, control circuitry 31, the internal memory circuit 32, an input circuit 33A, the display 34, and an image processing circuit 35. The image processing circuit 35 is composed of the FPGA or the like.

The input circuit 33A includes components similar to those of the input circuit 33 shown in FIG. 1. The input circuit 33A includes a switch that is operable by the operator and switches whether or not to perform image processing on multiple raw data to be subjected to position adjustment, in addition to the data acquisition start button, the data acquisition end button, and the switch for switching whether or not to correct the position data. In addition, a switch, such as a rotary switch, which can input information indicating whether or not to correct the position data, as well as information indicating whether or not to perform image processing on multiple raw data to be subjected to position adjustment may be provided.

The image processing circuit 35 performs image processing on the 2D image data (raw data or SC data) generated by the 2D image generation circuit 22. Examples of the image processing performed by the image processing circuit 35 include (1) histogram conversion processing, (2) speckle reduction processing, and (3) structure emphasizing processing.

Figure 9:
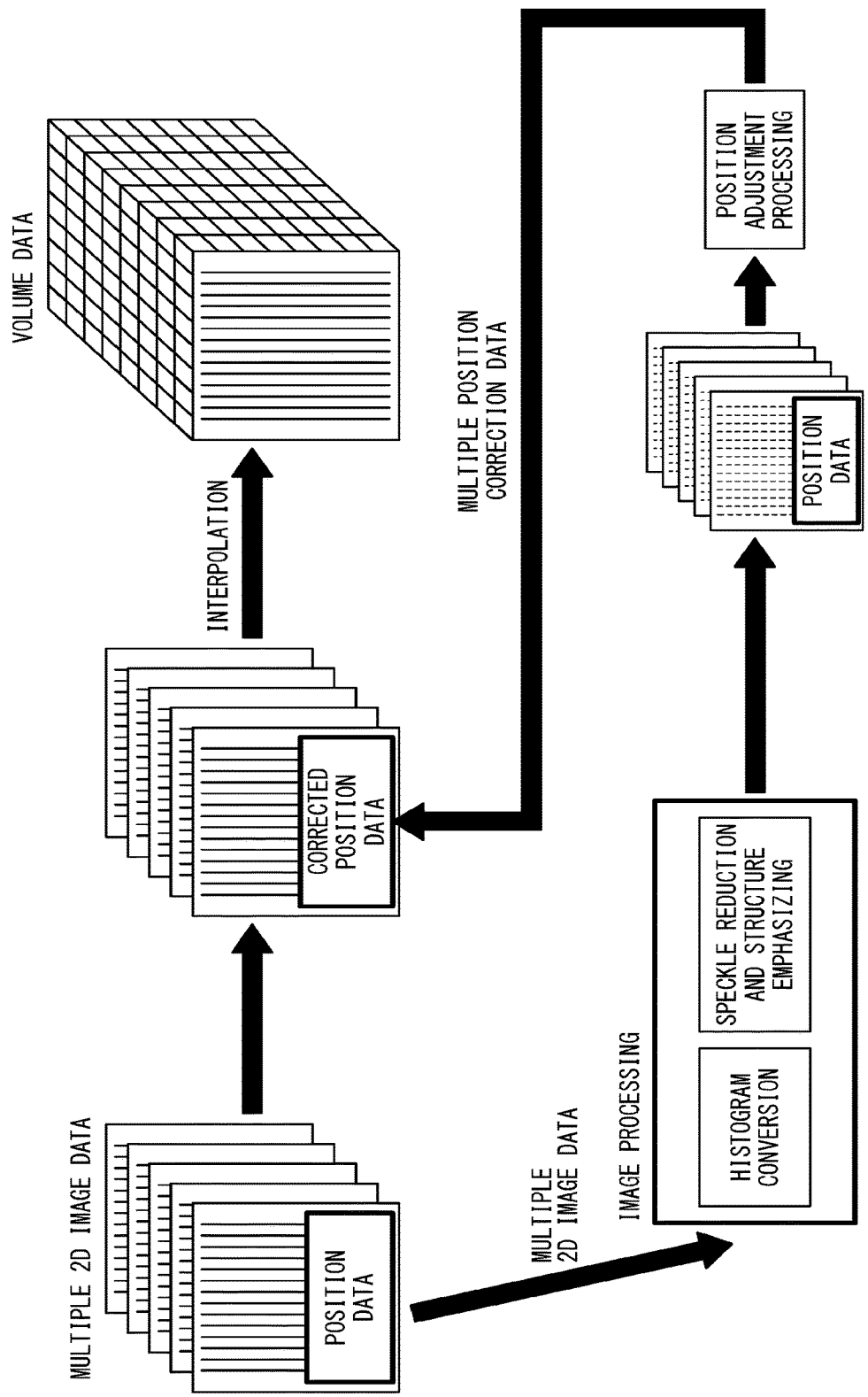
FIG. 9 is a conceptual diagram for explaining an outline of a position data correction method according to the ultrasonic diagnostic apparatus according to the second embodiment.

FIG. 9 is a conceptual diagram for explaining an outline of the position data correction method according to the ultrasonic diagnostic apparatus 10A.

As shown in FIG. 9, position data is attached to each of the 2D image data. Image processing is performed on each of the 2D image data. Next, position correction data for each of the 2D image data is calculated by performing position adjustment processing on each of the 2D image data which is obtained after the image processing and arranged in accordance with the attached position data. The position data attached to each of the 2D image data is corrected using the corresponding position correction data, and the position data attached to each of the multiple 2D image data is replaced by the corrected position data.

In the frame set as an origin in the position correct processing, raw data corresponding to the central frame may be used in the multiple raw data. Alternatively, raw data corresponding to a frame designated by the operator through the input circuit 33 may be used. The correction circuit 27 sequentially calculates the position correction data for the raw data corresponding to adjacent frames starting from the frame set as the origin.

The image processing performed by the image processing circuit 35, i.e., (1) histogram conversion processing, (2) speckle reduction processing, and (3) structure emphasizing processing will be sequentially described below.

(1) Histogram Conversion Processing

Figure 10A:
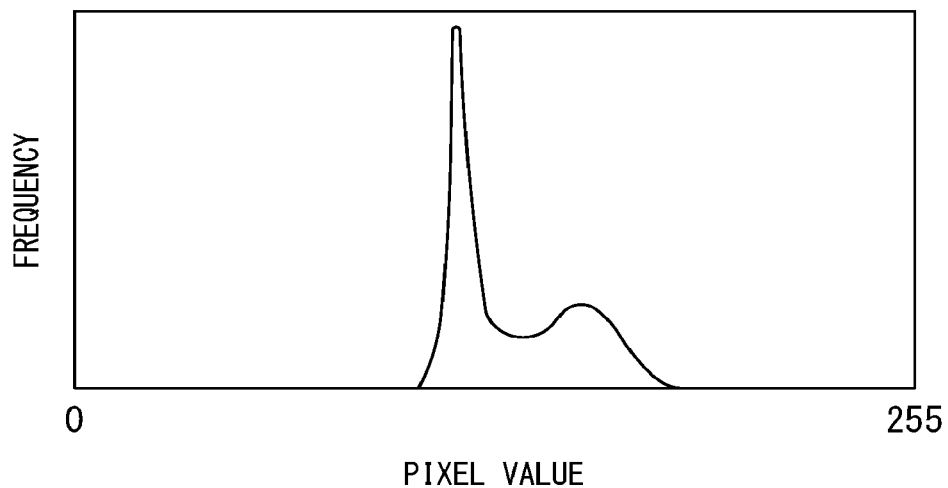
FIG. 10A is a diagram showing a histogram of 2D image data before a histogram conversion processing.
Figure 10B:
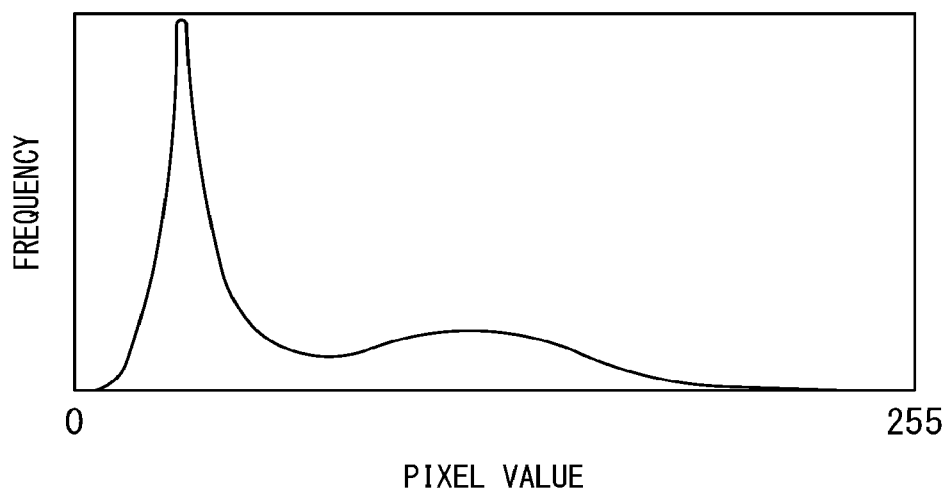
FIG. 10B is a diagram showing a histogram of 2D image data after a histogram conversion processing.

In 2D image data, when a distribution (for example, 100-200) in a pixel value is narrower than a display gradation (for example, 0-255), a grayscale difference is small and thus it is difficult to discriminate the image. In such a case, there is a possibility that the correction of the position data may be unsuccessful and a position gap may be large. In order to improve this, histogram conversion processing is performed on the original 2D image data, thereby optimizing the histogram of the 2D image data. FIGS. 10A and 10B are diagrams showing the histogram of the 2D image data before and after the histogram conversion processing.

Examples of the histogram conversion processing include conversion using a broken-line tone curve (a graph showing a gradation conversion function, which is a function for converting a pixel value, is referred to as a tone curve), gamma conversion using a gamma curve, and conversion using an S-shaped tone curve. The conversion by manually setting a tone curve is not practical, and thus the conversion is automated.

One method for the automation is a method of expanding a distribution by expanding the interval between a minimum value and a maximum value of a distribution of pixel values in which the frequency of the histogram shown in FIG. 10A is present, as shown in FIG. 10B. More preferably, the minimum value and the maximum value of the distribution of the pixel values are respectively matched with the minimum value and the maximum value of the display gradation. Another method for the automation is a method of converting the histogram shown in FIG. 10A into a designated distribution. For example, as a changed distribution shape, any distribution shape, such as a uniform distribution over the display gradation and a Gaussian distribution, can be used. The histogram conversion processing is not limited to these two methods.

Histogram conversion processing is performed on the 2D image data to optimize the histogram, thereby emphasizing a grayscale difference in an image with a simple configuration and facilitating the discrimination of a tissue or the like. Consequently, the accuracy of the subsequent correct processing for the position data can be improved. Thus, since a distortion in the 3D image to be displayed is reduced, the 3D image with a high diagnostic performance can be provided to a diagnostician.

(2) and (3) Speckle Reduction Processing and Structure Emphasizing Processing

The speckle reduction processing and the structure emphasizing processing are performed using a well-known technique, for example, a technique disclosed in Japanese Patent Laid-Open No. 2009-153918. This is a method using at least a non-linear anisotropic diffusion filter, multiresolution decomposition/composition, high-frequency component control processing, and a combination thereof.

The non-linear anisotropic diffusion filter performs isotropic diffusion processing (smoothing processing) on each bright point of 2D image data when bright points with no directivity, such as speckles, are distributed, and reduces the speckles in the 2D image data. On the other hand, in the case of a linear structure with high brightness, such as a vessel wall or a diaphragm, diffusion is performed in a direction along a line; diffusion is not substantially performed in a direction vertical to the line, or an edge is emphasized; the line is made clear without feathering; and the structure is emphasized.

In the multiresolution decomposition, the entire image data, which is 2D image data, is decomposed into partial image data having a high spatial frequency component and multiple partial image data having a low spatial frequency component, by using wavelet transform as a typical method. For example, when the size of the original entire image data is 512 pixels×512 pixels, the multiresolution decomposition enables decomposition of the entire image data into four pieces of partial image data (LL, LH, HL, HH) of 256 pixels×256 pixels. LL has low-frequency components in the longitudinal and horizontal directions. HH has high-frequency components in the longitudinal and horizontal directions. LH and HL have high-frequency components in one of the longitudinal and horizontal directions, and have low-frequency components in the other one of the longitudinal and horizontal directions. Each partial image data indicates an image corresponding to a half of the entire size of the original 2D image data (entire image). Further, the LL component is subjected to multiresolution decomposition to thereby obtain four pieces of partial image data (LLLL, LLLH, LLHL, LLHH) of 128 pixels×128 pixels. Further, multiresolution decomposition can also be performed.

Assume a case where four pieces of partial image data (LL, LH, HL, HH) of 256 pixels×256 pixels. Non-linear anisotropic diffusion filter processing is performed on the LL component to thereby perform speckle reduction and structure emphasis. High-frequency component control processing is performed on the LH, HL, and HH components by some method. The high-frequency component control processing is performed so as to reduce speckles in a soft tissue obtained by removing a structure part. To remove the structure part from an object to be processed, edge data extracted by performing non-linear anisotropic diffusion filter processing on the LL component is used. After a series of processing is performed on four pieces of partial image data, wavelet inverse transform is used as a typical method and the data is restored to the entire image data of 512 pixels×512 pixels by multiresolution composition. As a result, the image in which speckles are reduced and the structure is emphasized is obtained.

It is expected that the use of a combination of the non-linear anisotropic diffusion filter, multiresolution decomposition/composition, and high-frequency component control processing provides a higher effect than when the non-linear anisotropic diffusion filter is used alone. The non-linear anisotropic diffusion filter processing requires a lot of time. Accordingly, the processing time is improved by using the LL image which is smaller than the original entire image data.

Thus, the use of at least the non-linear anisotropic diffusion filter, multiresolution decomposition/composition, high-frequency component control processing, and a combination thereof makes it possible to reduce speckles and emphasize the structure. Accordingly, an adverse effect of a fluctuation in the position adjustment due to speckles is reduced and the accuracy of the position adjustment (calculation of the similarity measure between the reference projection image data and the floating projection image data) by clarifying the structure is improved. Consequently, the accuracy of the subsequent correction of the position data can be improved and a distortion in the 3D image to be displayed can be further reduced, thereby making it possible to obtain 3D image data with a high image quality and provide an ultrasonic diagnostic apparatus with a high diagnostic performance.

Figure 11A:
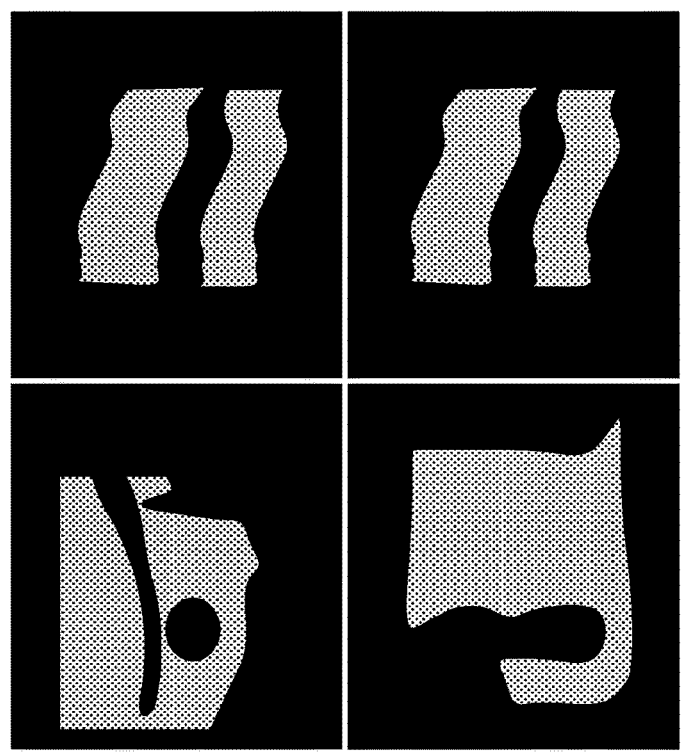
FIG. 11A is a diagram showing a display example of a 3D image by an ultrasonic diagnostic apparatus according to a related art.

FIG. 11A is a diagram showing a display example of a 3D image by an ultrasonic diagnostic apparatus according to a related art. FIG. 11B is a diagram showing a display example of a 3D image by the ultrasonic diagnostic apparatus 10A.

In each of FIGS. 11A and 11B, an upper-left figure shows an MPR image of an A-plane based on volume data; an upper-right figure shows an MPR image of a B-plane based on volume data; a lower-left figure shows an MPR image of a C-plane based on volume data; and a lower-right figure shows a volume rendering image base on volume data. In particular, when the MPR image of the B-plane shown in the upper-right figure of FIG. 11B is focused, a distortion in a tissue is considerably improved as compared to the MPR image of the B-plane shown in the upper-right figure of FIG. 11A, and thus the diagnostic performance is improved.

Next, the operation of the ultrasonic diagnostic apparatus 10A will be described with reference to FIGS. 8 and 12.

Figure 12:
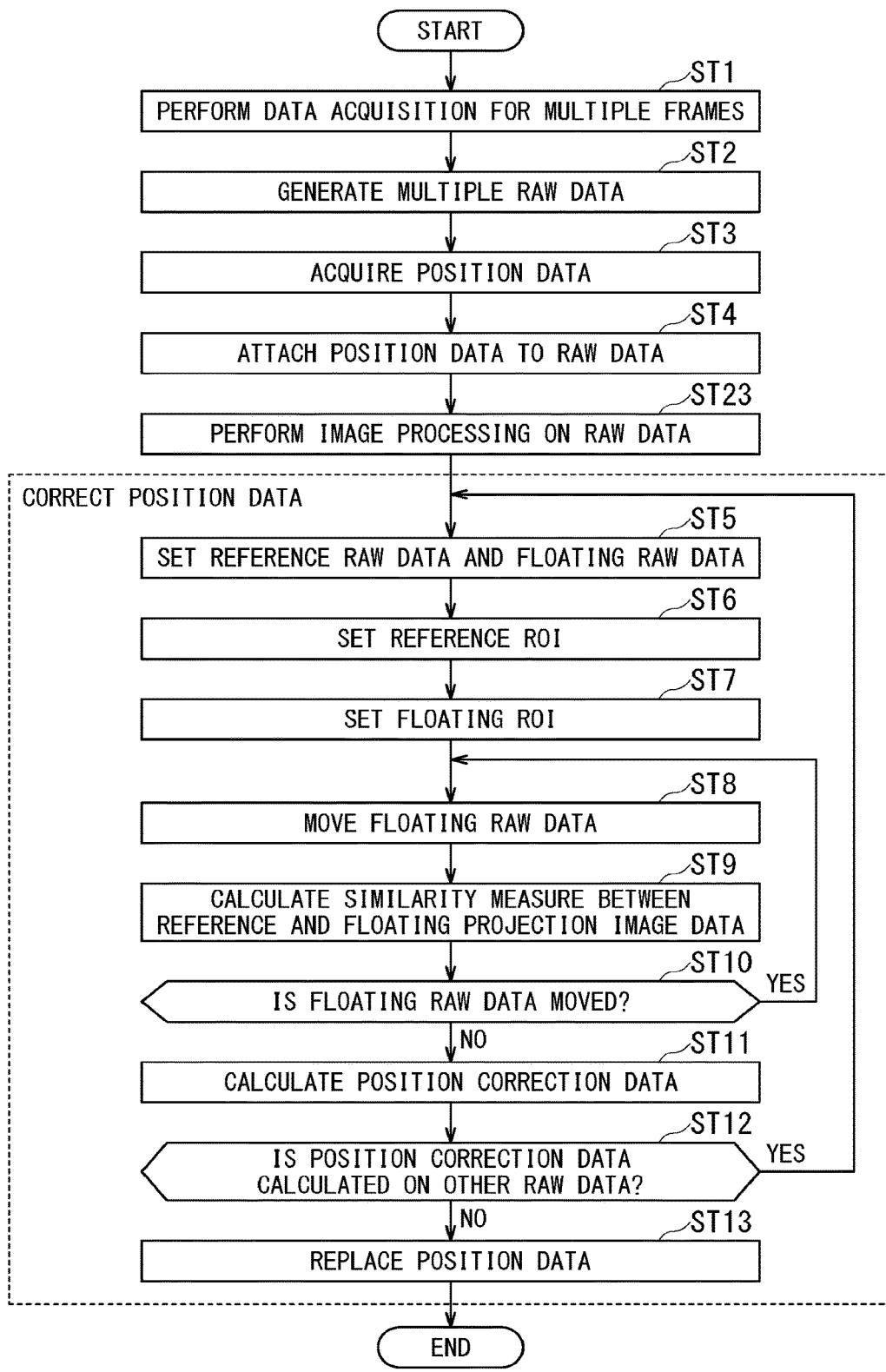
FIG. 12 is a flowchart showing an operation of the ultrasonic diagnostic apparatus according to the second embodiment.

FIG. 12 is a flowchart showing an operation of the ultrasonic diagnostic apparatus 10A.

The steps in FIG. 12 that are the same as those of the ultrasonic diagnostic apparatus 10 shown in FIG. 7 denoted by the same symbols, and descriptions thereof are omitted.

When the operator turns on the switch for switching whether or not to perform the image processing as the input circuit 33A, the image processing circuit 35 performs image processing on the raw data to which the position data is attached in step ST4 after step ST4 (step ST23). Examples of the image processing performed in step ST23 include (1) histogram conversion processing, (2) speckle reduction processing, and (3) structure emphasizing processing.

The ultrasonic diagnostic apparatus 10A arranges multiple raw data based on the position data associated with each of the multiple raw data, and performs position adjustment of two pieces of arranged raw data, thereby making it possible to appropriately correct the position data. The ultrasonic diagnostic apparatus 10A appropriately performs image processing on the multiple raw data to be subjected to position adjustment, thereby improving the accuracy of the correction of the position data.

3. FIRST MODIFIED EXAMPLE OF ULTRASONIC DIAGNOSTIC APPARATUS

According to the ultrasonic diagnostic apparatus 10 shown in FIG. 1, the attached position data is corrected and a tissue part included in each of the 2D image data is slid, the position of the tissue part can be appropriately adjusted. In addition, the ultrasonic diagnostic apparatus 10 can appropriately adjust a distortion in the tissue part included in each of the 2D image data. In this case, the correction circuit 27 performs the position data correction as described above, as well as the correction of a distortion in each of the 2D image data. Specifically, the correction circuit 27 performs the position data correction using the position correction data, while performing the distortion correction using distortion correction data on each of the 2D image data. During the operation to move the ultrasonic probe 11, when a force for pressing the ultrasonic probe 11 against an object is not uniform, a tissue of a living body in a region to be inspected is moved, which may result in deformation of the tissue, which is a soft tissue, of the living body. In this case, the correction circuit 27 performs the distortion correction. In particular, a distortion is likely to occur in an image of a mammary gland obtained by photographing, and thus the image is effective.

Methods for correcting a distortion include a method using linear conversion, a method using a distortion correction vector and a method using an image mosaicing. Further, the method using the distortion correction vector is divided into two methods. The method using the image mosaicing is divided into two methods.

First, the method using the linear conversion will be described.

The correction circuit 27 performs the linear conversion on the 2D image data on a second frame arranged in accordance with the attached position data, and considers the image data obtained after the linear conversion associated with the second frame as image data obtained before deformation of the soft tissue. The frame rate is several tens Hz, which is a high frame rate; a time difference between two frames is small; and deformation is not caused by intentionally applying a force. Accordingly, it is considered that the similarity measure of the soft tissue between the images of two adjacent frames is small, and thus linear conversion for correcting a distortion may be performed.

Specifically, the correction unit calculates the similarity measure as represented by the above Formula (1) or (2) between projection image data based on the 2D image data associated with the first frame (corresponding to reference projection image data shown in FIG. 6) and image data obtained after multiple linear conversion associated with the second frame (corresponding to floating projection image data shown in FIG. 6).

Examples of the linear conversion processing include enlarge/reduce, rotation, skew, and conversion processing using a combination thereof. Further, as described above, since it is considered that the similarity measure of the soft tissue between the 2D image data corresponding to two adjacent frames is small, the linear conversion processing may be limited to, for example, enlargement/reduction, to thereby simplify the processing.

Figure 13:
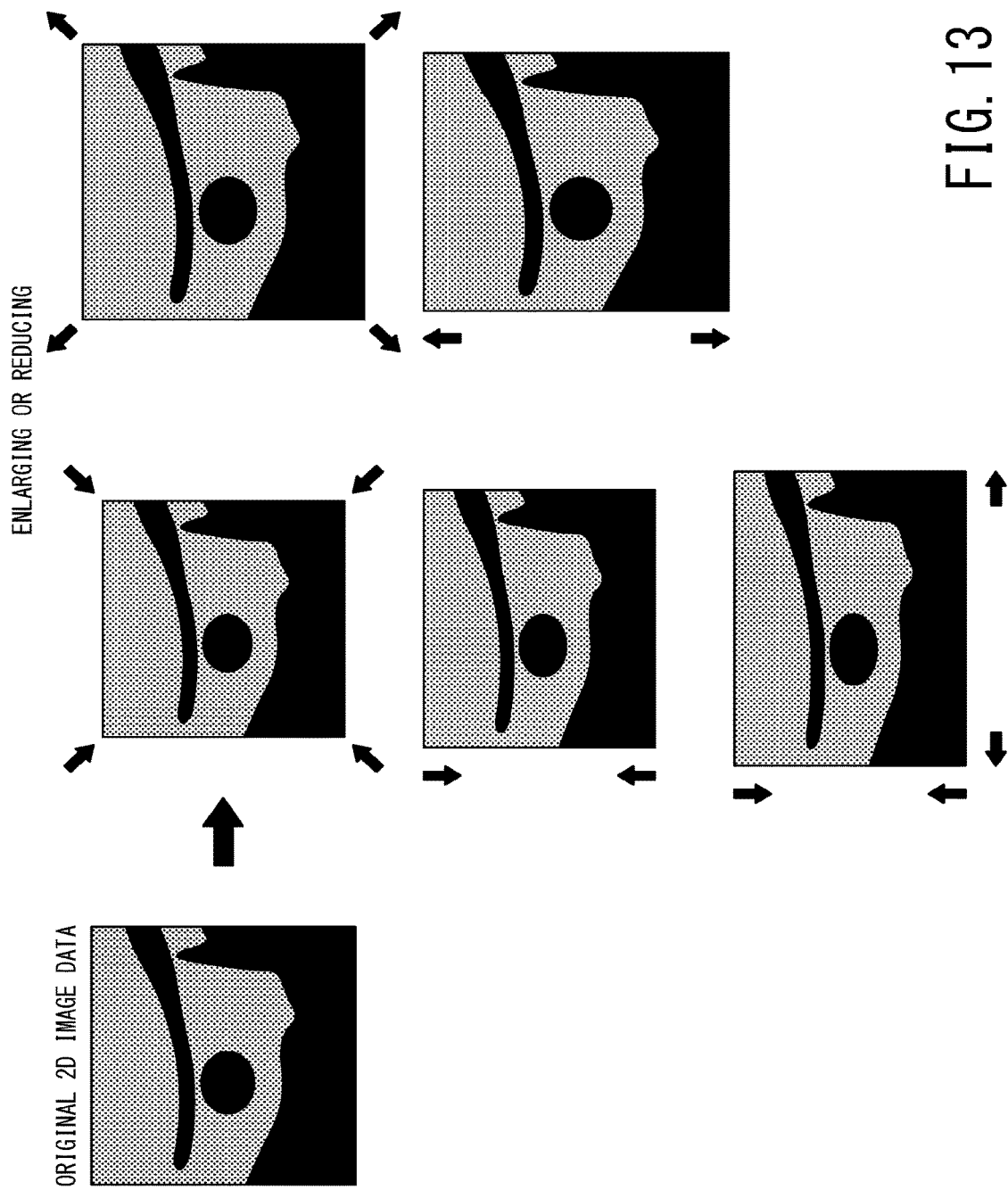
FIG. 13 is a diagram for explaining a linear conversion processing for the 2D image data.

FIG. 13 is a diagram for explaining the linear conversion processing for the 2D image data.

A figure on the left side of FIG. 13 shows an image based on the original 2D image data. A figure on the right side of FIG. 13 shows an image based on image data obtained after the original 2D image data is enlarged or reduced.

The linear conversion described above and the displacement of the floating raw data on the floating plane as described above with reference to FIG. 5 may be used in combination.

The linear conversion described above may be performed a plurality of times by changing the coefficient or processing format for the linear conversion. For example, processing including the displacement of the raw data is attempted for a plurality of types of linear conversions; the similarity measures are compared in each trial; and the displacement of the raw data and the linear conversion when the similarity measure is maximum are employed. In another example, the similarity measure is maximized by an optimization method, such as a gradient descent or a downhill simplex method, in which a state in which no linear conversion is performed is set as an initial state; the first linear conversion is performed and processing including the displacement of the raw data is attempted; the similarity measures of both data are compared to determine the coefficient or processing format for the subsequent linear conversion; and the similarity measure is gradually increased while performing reattempts, and the displacement of the raw data and the linear conversion when the similarity measure is maximum are employed.

Thus, the linear conversion processing is performed on the 2D image data, thereby making it possible to correct the position data and correct distortion data.

Next, the method using the distortion correction vector will be described.

The correction circuit 27 calculates the position correction data in the manner described above with reference to FIGS. 4A to 6. The position correction data indicates the extent and direction of the displacement between the position of floating raw data obtained before displacement and the position of floating raw data obtained when the similarity measure is high. The position correction data may also be referred to as a displacement vector. As shown in FIG. 4B, multiple reference ROIs may be set on the reference raw data. When multiple reference ROIs are set, a position correction data element, i.e., a displacement vector for each ROI, is obtained for each reference ROI. Each of the multiple ROIs is referred to as a ROI element. A value obtained by subtracting the position correction data, i.e., the ROI entire displacement vector, from the displacement vector of the ROI element is referred to as a distortion correction vector of the ROI element. When the distortion correct processing is performed by the following first method and second method, multiple reference ROIs are set. The number, position, shape, and the like of reference ROIs used when the position correction data is obtained need not necessarily match the number, position, shape, and the like of reference ROIs used when the distortion correct processing is performed. For example, one reference ROI may be used when the position correction data is obtained, and 20 reference ROIs may be used when the distortion correct processing is performed.

First, the first method for performing the distortion correction using the distortion correction vector for each of the 2D image data will be described. In the first method, a displacement vector pi at each point (pixel) is calculated, and a distortion correction vector di at each point is obtained by subtracting the displacement vector P from the displacement vectors.

Figure 14A:
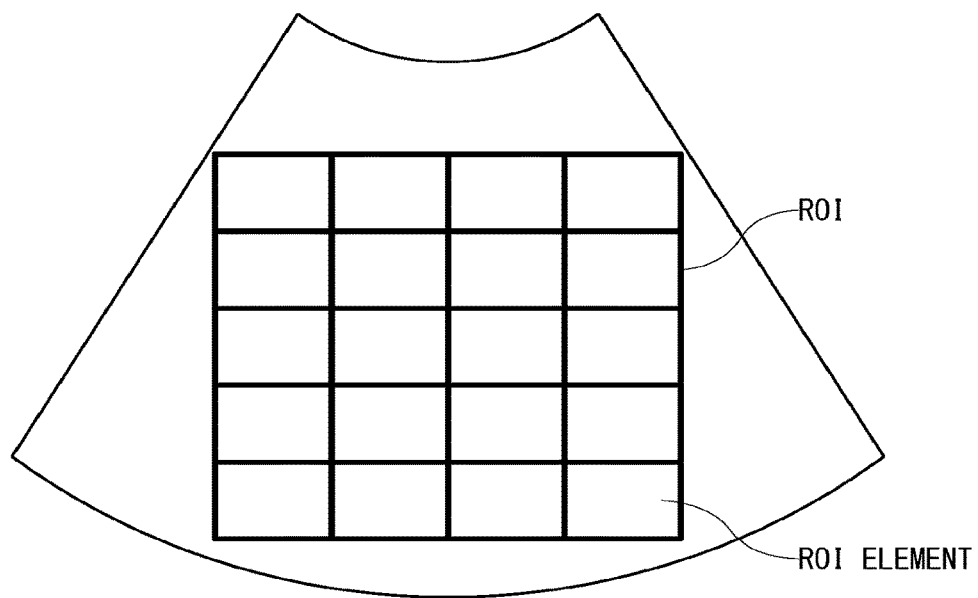
FIGS. 14A and 14B are diagrams for explaining a distortion correct processing.
Figure 14B:
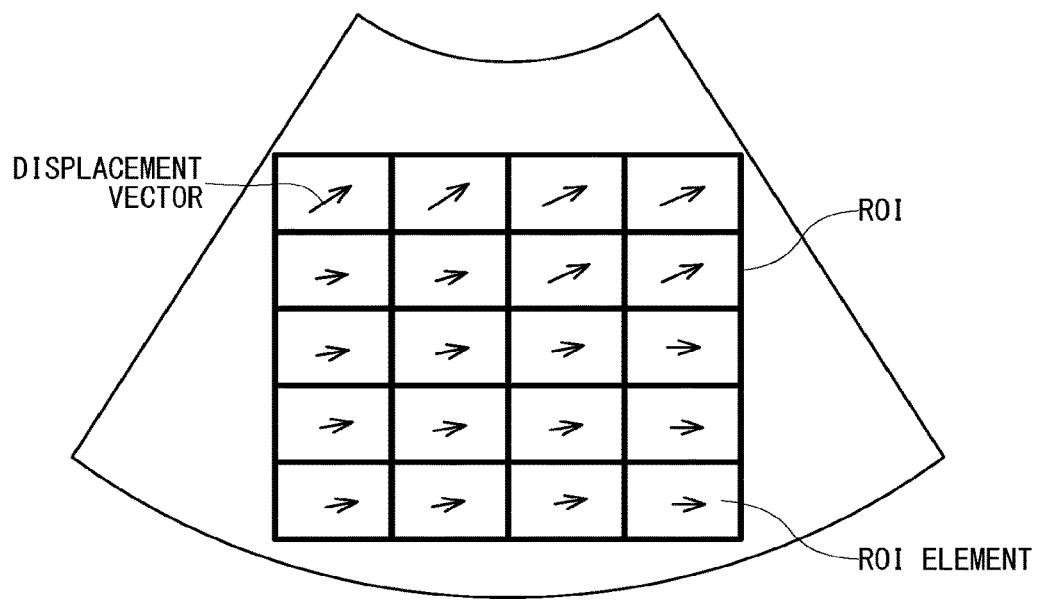
Figure 15:
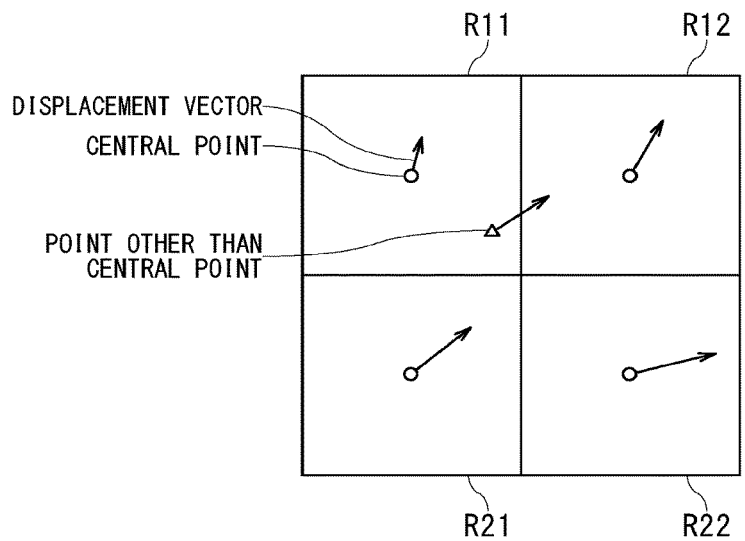
FIG. 15 is a diagram for explaining the distortion correct processing.

FIGS. 14A to 15 are diagrams for explaining the distortion correct processing.

Raw data corresponding to two frames is selected from multiple raw data. As shown in FIG. 14A, one ROI is set on one of the pieces of raw data corresponding to two frames. FIG. 14A shows a case where the ROI has a rectangular shape. However, the shape of the ROI is not limited to the rectangular shape.

In the ROI, a plurality of ROI elements, for example, 20 ROI elements, are set. The displacement vectors (shown in FIG. 14B) for the 20 ROI elements, respectively, are obtained. These displacement vectors are each considered to be a displacement vector at a central point in each ROI element.

FIG. 15 shows four ROI elements R11, R12, R21, and R22 which are extracted from 20 ROI elements shown in FIG. 14B. In the four ROI elements R11, R12, R21, and R22, the displacement vector at each point (pixel) other than the central point is obtained by interpolation processing from multiple displacement vectors associated with surrounding multiple ROI elements. For example, the displacement vector at a point (indicated by a triangular mark in the figure) other than the central point in the ROI element R11 is calculated by interpolation processing based on the displacement vector associated with four central points (indicated by a circle in the figure) in the four ROI elements R11, R12, R21, and R22. As the interpolation processing, linear interpolation (bilinear interpolation) or 3D interpolation (bicubic interpolation) is employed.

In this manner, the correction circuit 27 calculates, as the displacement vector pi at each point in the raw data, the displacement vector at the central point (indicated by a circle in FIG. 15) in each ROI element and the displacement vector at each point (indicated by a triangular mark in FIG. 15) other than the central point. Further, the distortion correction vector at each point in the raw data is calculated by di=pi–P as the distortion correction data about the raw data, and the distortion correction vector is applied to the raw data.

The correction circuit 27 may omit, as needed, the calculation of the displacement vector at each point other than the central point so as to reduce the calculation time. For example, the correction circuit 27 calculates one displacement vector at a plurality of adjacent points, instead of calculating one displacement vector at each point (pixel), in each ROI element. Alternatively, when the values of all displacement vectors at all central points are equal to or less than a threshold (or less than a threshold) in multiple continuous ROI elements, the correction circuit 27 does not calculate the displacement vector at each point other than the central point in each of the multiple ROI elements. The value of the displacement vector at each point in each ROI element is set as the value of the displacement vector at the central point in the ROI element. In another alternative, when the values of all displacement vectors at the central point in all ROI elements in one frame are equal to or less than the threshold, the correction circuit 27 does not calculate the displacement vector at each point other than the central point in the frame. The value of the displacement vector at each point in each ROI element is set as the value of the displacement vector at the central point in the ROI element.

According to the first method, the interpolation processing is performed using a displacement vector larger than a distortion correction vector, which leads to an increase in a resistance to noise.

Next, a second method for correcting a distortion using a distortion correction vector for each of the 2D image data will be described. The correction circuit 27 calculates the position correction data, i.e., the displacement vector P for the entire ROI. Next, displacement vectors p1, p2, ..., p20 for 20 ROI elements shown in FIG. 14B are calculated. From the displacement vectors, distortion correction vectors used as the distortion correction data for 20 ROI elements are calculated as d1=p1–P, d2=p2–P, ..., d20=p20–P. The distortion correction vectors d1, d2, ..., d20 are considered to be the distortion correction vectors at the central point in each ROI element. The interpolation processing performed by the first method on the displacement vectors is applied to each of the distortion correction vectors, and the distortion correction vector di at each point (pixel) other than the central point is calculated from the distortion correction vectors d1, d2, ..., d20.

According to the second method, since there is no need to calculate the distortion correction vector for each point, a time required for correct processing can be reduced.

In the first method and the second method, the position data correction may be performed again using the 2D image data subjected to distortion correction.

Next, the method using the image mosaicing will be described.

In the image mosaicing, the 2D image data is geometrically transformed by the following procedures (a) to (c). Various approaches to the image mosaicing have been developed.

(a) Feature point detection and matching
(b) Estimation of geometric transformation
(c) Geometric transform of image Various geometric transformations are conceivable, but here we describe a method that uses a projective transformation and a method that uses displacement vectors and distortion correction vectors.

In the method using the projective transformation, in the above (a), the correction circuit 27 detects feature points from each of two raw data that are the reference raw data and the floating raw data. Next, the correction circuit 27 performs correspondence (matching) between the two raw data based on the detected feature points.

Figure 16:
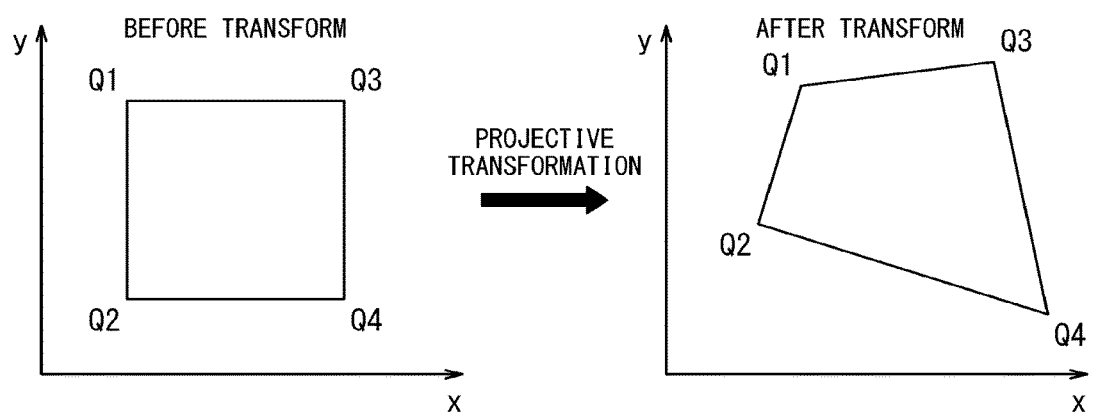
FIG. 16 is a diagram for explaining a projective transformation processing.

In the above (b) following the above (a), the correction circuit 27 uses the projective transformation as a general transformation rather than the above-mentioned linear conversion, the projective transformation being a geometric transformation. As shown in FIG. 16, the projective transformation is a transformation such that an arbitrary quadrangle composed of points Q1 to Q4 is shifted to the other arbitrary quadrangle. In the projective transformation, displacement of the image data is included, the linearity of the line segment is maintained but the parallelism is lost. The correction circuit 27 can calculate (a value of) the projective transformation based on coordinates of the corresponding feature points of the two pieces of raw data.

In the above (c) following the above (b), the correction circuit 27 converts the image data by using the projective transformation on the floating raw data for performing the distortion correction.

On the other hand, in the method using the displacement vectors or the distortion correction vectors, the correction circuit 27 associates feature points by detecting and matching the feature points of the reference raw data and the floating raw data. This correspondence can be regarded as the above displacement vectors. Accordingly, similarly to the above-described method using the displacement vectors and the distortion correction vectors, the correction circuit 27 calculates the displacement vectors and the distortion correction vectors of points other than the feature points based on interpolating displacement vectors or distortion correction vectors of neighboring feature points, and converts the image data.

According to the method using the image mosaicing, processing is more complicated than the method using the linear conversion, but highly accurate distortion correction is possible.

In this manner, by applying the image mosaicing to the 2D image data, the position data can be corrected and the distortion data can be corrected.

As described above, since a distortion in the 3D image displayed by the method using the linear conversion, the method using the distortion correction vector or the image mosaicing can be reduced, the 3D image with a high diagnostic performance can be provided to a diagnostician.

Figure 17:
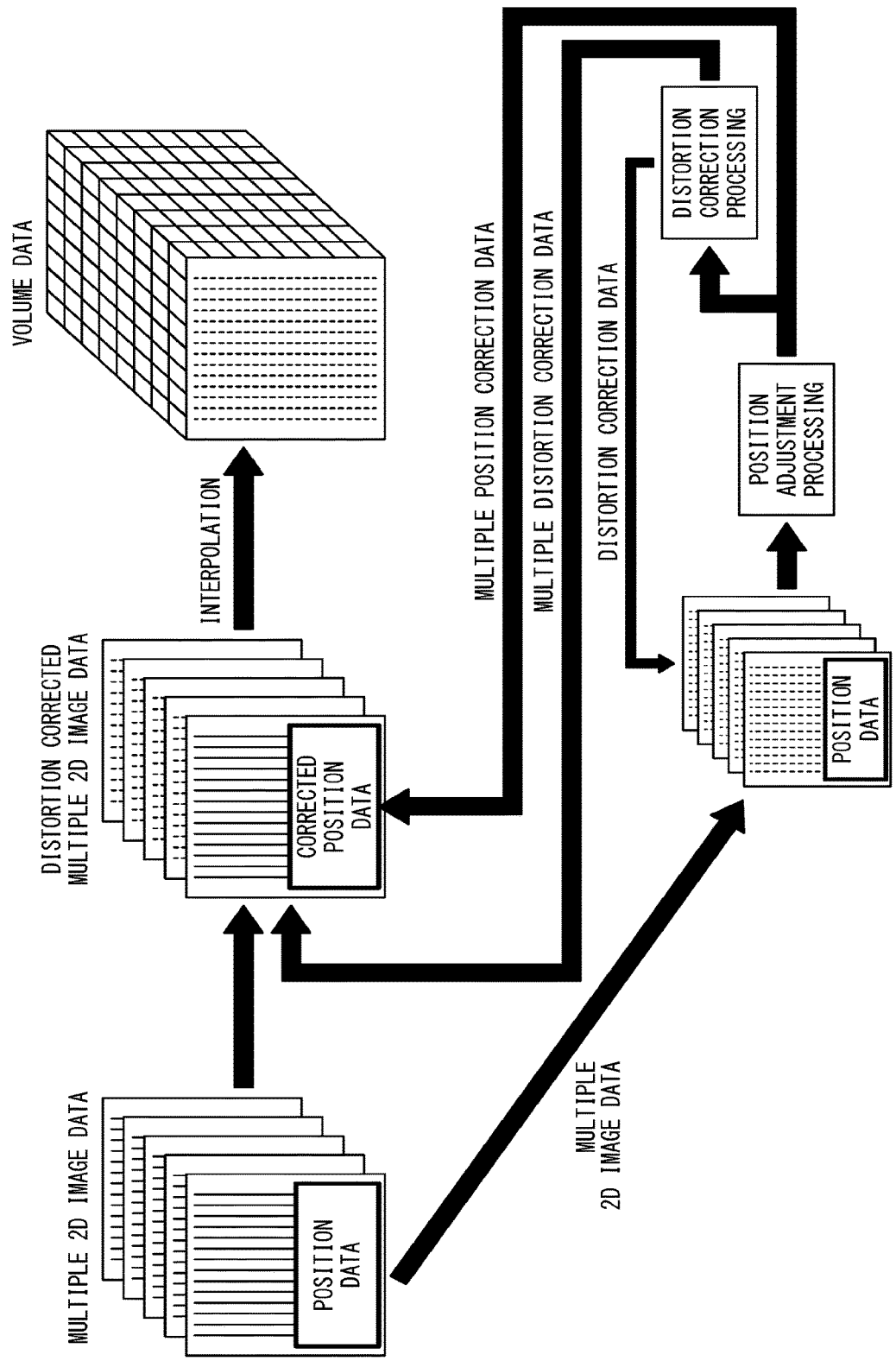
FIG. 17 is a conceptual diagram for explaining an outline of the method using the correction of the position data attached to the 2D image data and the correction of a distortion in the 2D image data in the ultrasonic diagnostic apparatus according to the first embodiment.

FIG. 17 is a conceptual diagram for explaining an outline of the method using the correction of the position data attached to the 2D image data and the correction of a distortion in the 2D image data in the ultrasonic diagnostic apparatus 10.

As shown in FIG. 17, position data is attached to each of the 2D image data. The position adjustment processing is performed on each of the 2D image data arranged in accordance with the attached position data, thereby calculating the position correction data for each of the 2D image data. When the position data attached to each of the 2D image data is corrected using the corresponding position correction data, the position data attached to each of the multiple 2D image data is replaced by the corrected position data.

After the position data is corrected, or in parallel to the correction of the position data, the distortion correct processing is performed on each of the 2D image data arranged in accordance with the attached position data, thereby calculating the distortion correction data for each of the 2D image data. Each of the 2D image data is corrected using the distortion correction data.

In the frame set as an origin in the distortion correct processing, raw data corresponding to the central frame in the multiple raw data is used. Alternatively, raw data corresponding to a frame designated by the operator through the input circuit 33 is used as the frame set as the origin. The correction circuit 27 sequentially calculates the distortion correction data about the raw data corresponding to adjacent frames starting from the frame set as the origin.

The above embodiments show a case where the distortion correct processing is applied to the ultrasonic diagnostic apparatus 10 shown in FIG. 1. However, the distortion correct processing can also be applied to the ultrasonic diagnostic apparatus 10A shown in FIG. 8. Specifically, the position adjustment processing and distortion correct processing shown in FIG. 17 may be performed on each of the 2D image data that is obtained after image processing and arranged in accordance with the attached position data.

4. SECOND MODIFIED EXAMPLE OF ULTRASONIC DIAGNOSTIC APPARATUS

According to the ultrasonic diagnostic apparatus 10 shown in FIG. 1, the position correct processing can be performed on the position data about each of the 2D image data obtained by transmitting and receiving ultrasonic waves in a 2D imaging region while the operator moves the 1D array probe (shown in FIG. 2A) as the ultrasonic probe 11. However, in the ultrasonic diagnostic apparatus 10, a mechanical 4D probe (shown in FIG. 2B) and a 2D array probe (shown in FIG. 2C), which are capable of photographing multiple scan planes, may be used as the ultrasonic probe 11.

In this case, the ultrasonic diagnostic apparatus 10 performs the position correct processing on the position data about each volume data obtained by transmitting and receiving ultrasonic waves in a 3D imaging region while the operator moves the mechanical 4D probe or the 2D array probe, and generates composite volume data from multiple volume data. The multiple volume data may be generated while the operator moves the 1D array probe (shown in FIG. 2A).

Figure 18:
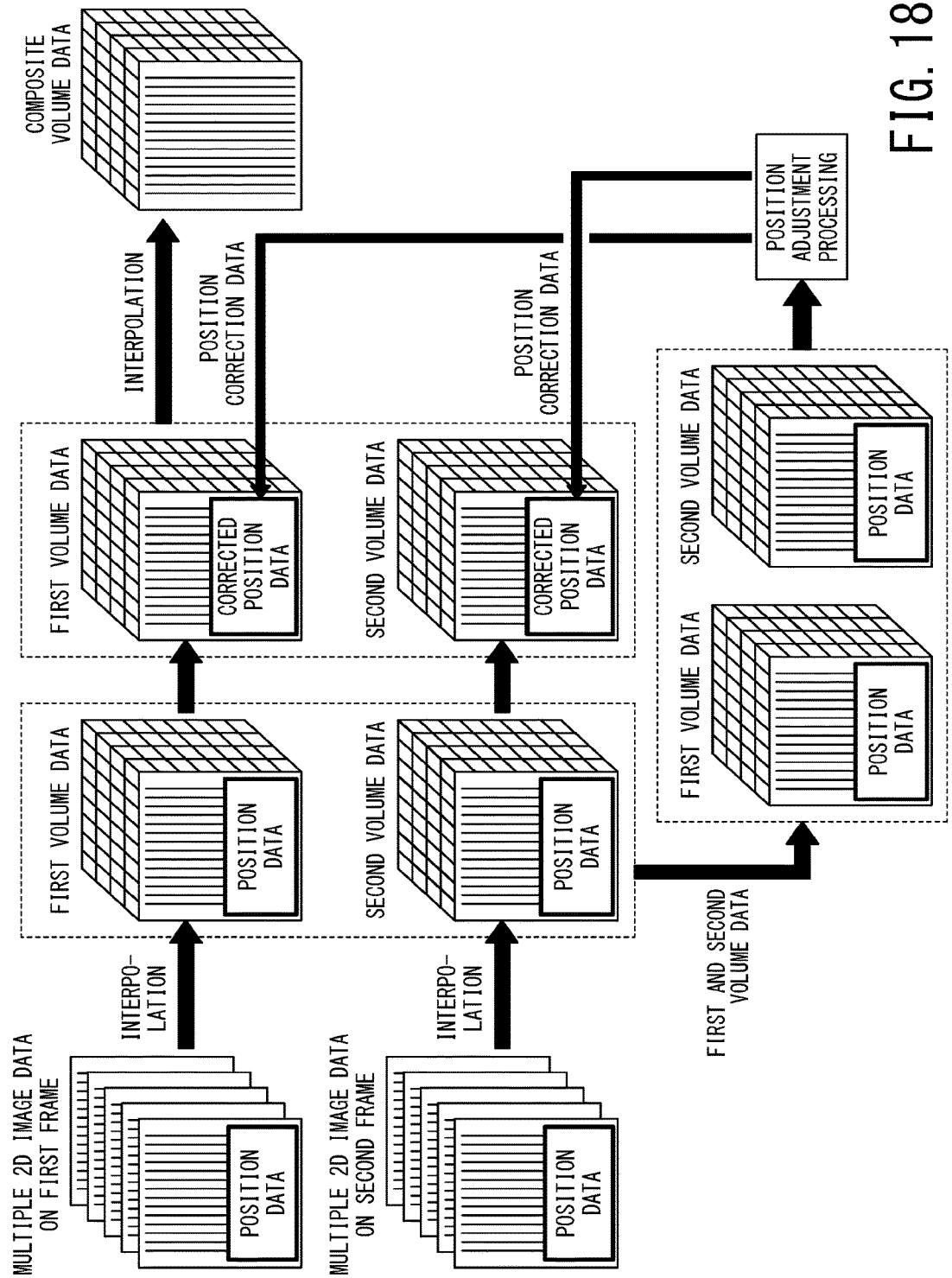
FIG. 18 is a conceptual diagram for explaining an outline of the method for correcting the position data attached to the volume data in the ultrasonic diagnostic apparatus according to the first embodiment.

FIG. 18 is a conceptual diagram for explaining an outline of the method for correcting the position data attached to the volume data in the ultrasonic diagnostic apparatus 10.

As shown in on the left side of the FIG. 18, position data is attached to each of the 2D image data (raw data or SC data) associated with the first frame. Position data is attached to each of the 2D image data (raw data or SC data) associated with the second frame.

The interpolation processing is performed on each of the 2D image data associated with the first frame, thereby generating first volume data associated with the first frame. The interpolation processing is performed on each of the 2D image data associated with the second frame, thereby generating second volume data associated with the second frame.

In this case, the position data about the first volume data indicates a representative value of multiple position data respectively attached to multiple 2D image data based on which the first volume data is generated. The position data attached to each of the 2D image data based on which the first volume data is generated is geometrically calculated from the position data about the ultrasonic probe 11. To obtain the representative value, various measures for obtaining an appropriate value can be taken. For example, simple calculation of an average value, as well as calculation of an average value by eliminating a value which is apart from another value by a certain value or more, and taking a median. The same holds true for the position data about the second volume data.

The position adjustment processing is performed on each of the volume data arranged in accordance with the attached position data, thereby calculating the position correction data for each volume data. When the position data attached to each volume data is corrected using the corresponding position correction data, the position data attached to each of the multiple volume data is replaced by the corrected position data.

The position adjustment processing for synthesizing two volume data so as to generate composite volume data will now be described.

Figure 19A:
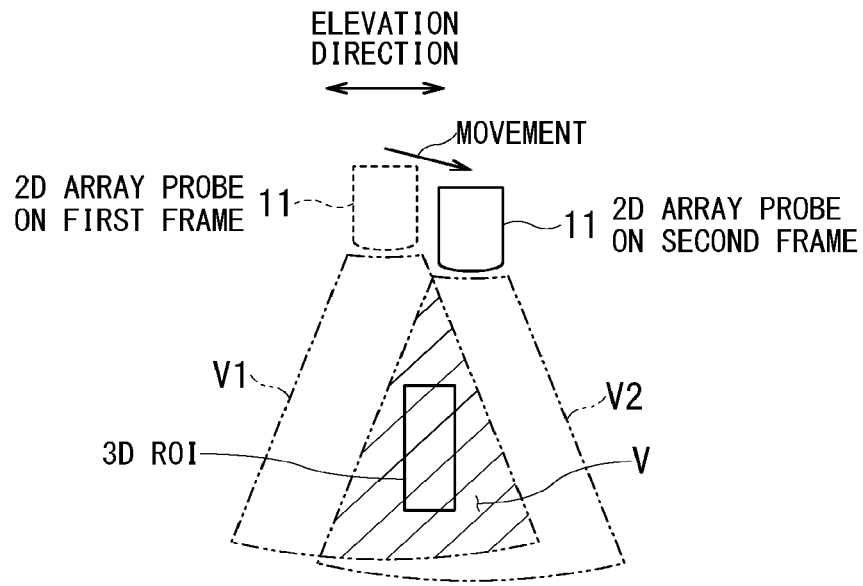
FIGS. 19A and 19B are conceptual diagrams for explaining the position adjustment processing for synthesizing two pieces of volume data.
Figure 19B:
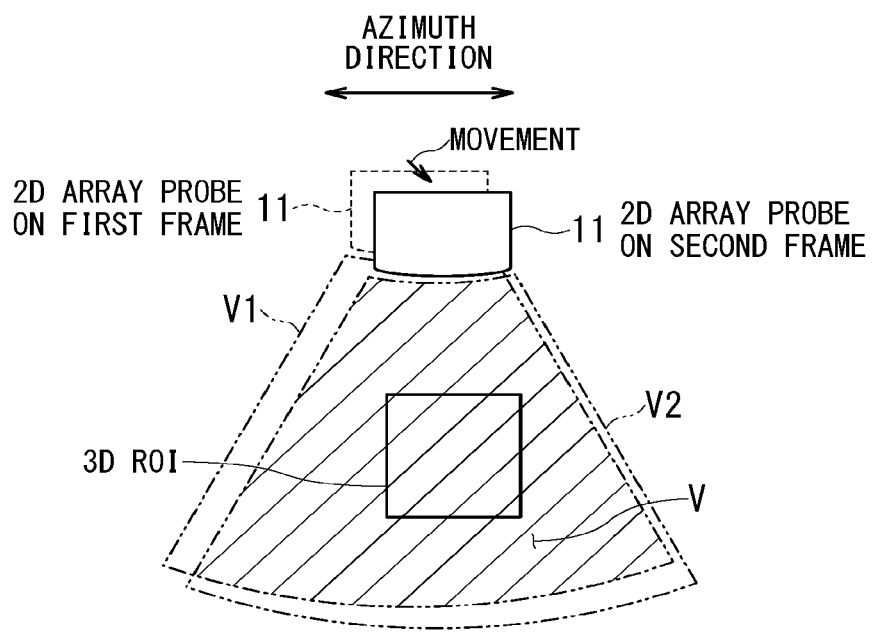

FIGS. 19A and 19B are conceptual diagrams for explaining the position adjustment processing for synthesizing two pieces of volume data.

FIG. 19A is a side view of the 2D array probe 11 before and after the movement by the operator. FIG. 19B is a front view of the 2D array probe 11 before and after the movement by the operator. FIGS. 18A and 18B show first volume data V1, second volume data V2, and a 3D superimposing region V for the first and second volume data.

One (or multiple) 3D ROI is set in the 3D superimposing region V in the first volume data V1. When the 3D ROI is set in the 3D superimposing region V by using the first volume data V1, the 3D ROI is also set in the second volume data V2.

The second volume data V2 is three-dimensionally moved (parallel displacement and rotational displacement) in the state where the 3D ROI is fixed, and the image in the fixed 3D ROI is changed. Multiple partial data to be moved in the 3D ROI based on the second volume data V2 is obtained. For each of multiple partial data to be moved, the similarity measure with the partial data to be referred to in the 3D ROI of the first volume data V1 is calculated, and the similarity measures are compared. The partial data to be moved when the similarity measure is maximum (value is minimum) is considered to be matched with the partial data to be referred to. Further, the amount of displacement to the second volume data associated with the partial data to be moved when the similarity measure is maximum is calculated as the position correction data for the second volume data V2 from the initial second volume data obtained before displacement.

As the frame set as the origin in the position correct processing, volume data corresponding to the central frame in multiple volume data is used. Alternatively, volume data corresponding to a frame designated by the operator through the input circuit 33 is used as the frame set as the origin. The correction circuit 27 sequentially calculates the position correction data for the volume data corresponding to adjacent frames starting from the frame set as the origin. The present invention is not limited to the case where correction circuit 27 generates composite volume data by using the entire multiple volume data. When the movement rate of the probe moved by the operator is lower than the movement rate of scanning using volume data, three or more pieces of volume data are present at one point. The correction circuit 27 may generate composite volume data by using two pieces of adjacent volume data among the three or more pieces of volume data.

In this case, the correction circuit 27 uses 2D image data corresponding to the central scan plane in the multiple 2D image data based on which each volume data is generated. The correction circuit 27 performs the position adjustment processing on two pieces of adjacent volume data by the method shown in FIGS. 19A and 19B. The correction circuit 27 obtains, by interpolation processing, data between two pieces of 2D image data corresponding to two central scan planes obtained after position adjustment, and generates composite volume data based on the two pieces of 2D image data corresponding to the two central scan planes obtained after position adjustment and the data obtained by interpolation processing. Such interpolation processing can be performed because the movement rate of the probe is low and the two central scan planes are in proximity to each other.

Alternatively, the correction circuit 27 may obtain data between two central scan planes obtained after position adjustment, by first volume data V1, second volume data V2, or may obtain the data by synthesizing the first volume data V1 and the second volume data V2.

Further, when the movement rate of the probe moved by the operator is lower than the movement rate of scanning using volume data, a large number of pieces of volume data are present at one point. However, not all the volume data is required for one point, and at least two pieces of volume data are required. In such a case, the transmitting and receiving circuit 21 can control one point to fall within a range of two or less pieces of adjacent volume data by reducing the tilt angle (amplitude) of the scan plane of the 2D array probe (or the mechanical 4D probe). By this control, the volume rate for generating composite volume data is increased, which leads to an improvement in real-time performance. The tilt angle of the scan plane may be determined based on a normal movement rate obtained through clinical experiences, may be designated by the operator through the input circuit 33, or may be automatically set based on the movement rate of the 2D array probe that is obtained from the position data detected by the sensor 13. This control performed by the transmitting and receiving circuit 21 is combined with the generation of the composite volume data described above, thereby making it possible to efficiently generate composite volume data.

While the above embodiments show an example in which the correct processing for position data attached to volume data is applied to the ultrasonic diagnostic apparatus 10 shown in FIG. 1. However, the correct processing for position data attached to volume data may be applied to the ultrasonic diagnostic apparatus 10A shown in FIG. 8.

5. MEDICAL IMAGE PROCESSING APPARATUS ACCORDING TO PRESENT EMBODIMENT

Figure 20:
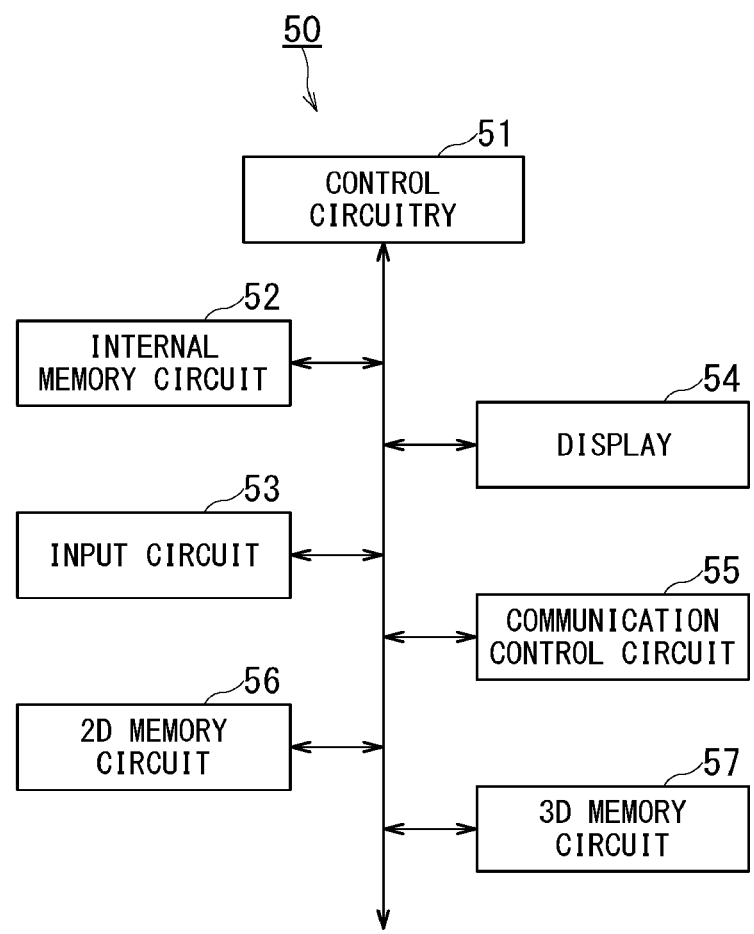
FIG. 20 is a schematic diagram showing a configuration of a medical image processing apparatus according to a present embodiment.

FIG. 20 is a schematic diagram showing a configuration of a medical image processing apparatus according to a present embodiment.

FIG. 20 shows a medical image processing apparatus 50 according to the present embodiment. The medical image processing apparatus 50 is, for example, a medical image management device (image server), which is not shown, a workstation, or a diagnostic reading terminal, which is not shown, and is provided on a medical image system connected via a network. The medical image processing apparatus 50 may be an offline device.

The medical image processing apparatus 50 includes control circuitry 51, an internal memory circuit 52, an input circuit 53, a display 54, a communication control circuit 55, a 2D memory circuit 56, and a 3D memory circuit 57.

The control circuitry 51 has a configuration similar to that of the control circuitry 31 shown in FIG. 1. The control circuitry 51 reads out a program which is stored in the internal memory circuit 52 or is directly incorporated into the control circuitry 51, and executes the program, thereby comprehensively controlling the processing operation of the units 52 to 57.

The internal memory circuit 52 has a configuration similar to that of the internal memory circuit 32 shown in FIG. 1. The internal memory circuit 52 stores various processing programs used in the control circuitry 51 and data necessary for executing the programs. The OS may include a GUI capable of performing basic operations by the input circuit 53 by making great use of graphics for a display of information for the operator on the display 54.

The input circuit 53 has a configuration similar to that of the input circuit 33 shown in FIG. 1. When the input device is manipulated by the operator, the input circuit 53 generates an input signal according to the manipulation and outputs the input signal to the control circuitry 51. The medical image processing apparatus 50 may include a touch panel having a configuration in which the input device is integrated with the display 54.

The display 54 has a configuration similar to that of the display 34 shown in FIG. 1. The display 54 displays 3D image data and the like generated by the control of the control circuitry 51 as a 3D image.

The communication control circuit 55 includes a connector using a combination of a parallel connection specification and a serial connection specification. The communication control circuit 55 has a function capable of performing a communication control according to the specifications and connecting to a network through a telephone line. With this configuration, the medical image processing apparatus 50 is connected to the network.

The 2D memory circuit 56 has a configuration similar to that of the 2D memory circuit 23 shown in FIG. 1. The 2D memory circuit 56 stores multiple 2D image data. The multiple 2D image data are transmitted through the communication control circuit 55, and position data is attached to each piece of the multiple 2D image data.

The 3D memory circuit 57 has a configuration similar to that of the 3D memory circuit 29 shown in FIG. 1, and stores the volume data generated by the control circuitry 51.

Next, functions of the medical image processing apparatus 50 according to the present embodiment will be described.

Figure 21:
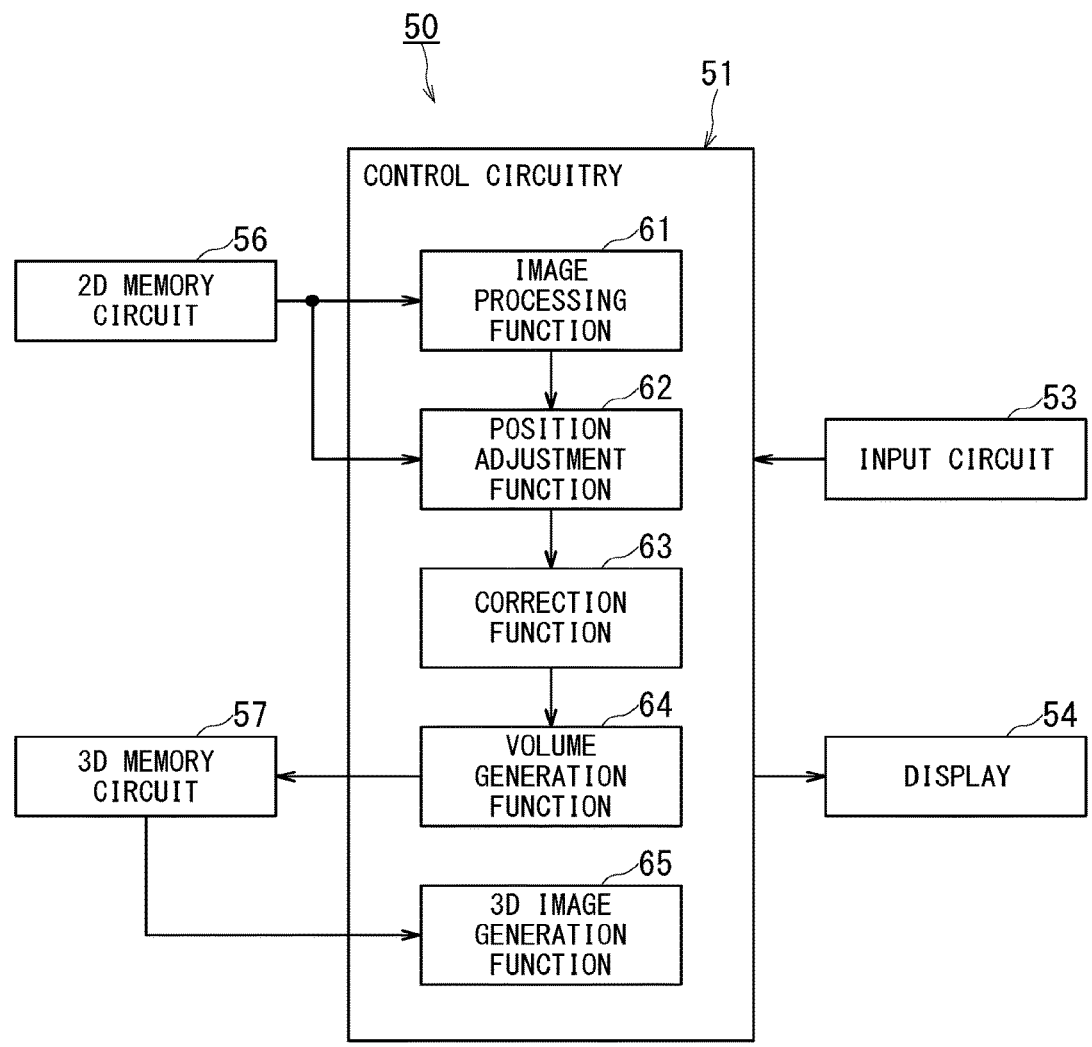
FIG. 21 is a block diagram showing functions of the medical image processing apparatus according to the present embodiment.

FIG. 21 is a block diagram showing functions of the medical image processing apparatus 50 according to the present embodiment.

The control circuitry 51 executes programs, and the medical image processing apparatus 50 functions as an image processing function 61, a position adjustment function 62, a correction function 63, a volume generation function 64, and a 3D image generation function 65. A case where the functions 61 to 65 function as software will be described by way of example. However, all or some of the functions 61 to 65 may be provided in the medical image processing apparatus 50 as hardware.

The image processing function 61 has a function similar to the function performed by the image processing circuit 35 shown in FIG. 8.

The position adjustment function 62 has a function similar to the function performed by the position adjustment circuit 26 shown in FIG. 1 or 8. The position adjustment function 62 performs the position adjustment based on the multiple raw data processed by the image processing function 61 or based on the non-processed multiple raw data.

The correction function 63 has a function similar to the function performed by the correction circuit 27 shown in FIG. 1 or 8.

The volume generation function 64 has a function similar to the function performed by the volume generation circuit 28 shown in FIG. 1.

The 3D image generation function 65 has a function similar to the function performed by the 3D image generation circuit 30 shown in FIG. 1.

The medical image processing apparatus 50 arranges multiple raw data based on position data associated with each of the multiple raw data, and performs position adjustment of two pieces of arranged raw data, thereby making it possible to appropriately correct the position data. Further, the medical image processing apparatus 50 appropriately performs the image processing on the multiple raw data to be subjected to position adjustment, thereby making it possible to improve the accuracy of the position data.

According to the ultrasonic diagnostic apparatus and the medical image processing apparatus of at least one of the embodiments described above, it is possible to appropriately correct the multiple position data of the multiple 2D image data.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
    a transmitting and receiving circuit configured to transmit an ultrasonic wave to an ultrasonic probe and receive a signal based on the ultrasonic wave received by the ultrasonic probe;
    a generation circuit configured to generate multiple 2D image data in a chronological order based on the signal;
    an acquisition circuit configured to acquire three-dimensional multiple position data of the ultrasonic probe;
    an associating circuit configured to associate the multiple position data with the respective multiple 2D image data; and
    a correction circuit configured to correct the multiple position data associated by the associating circuit, wherein the correction circuit is configured to
        set a projection plane between two pieces of the multiple 2D image data,
        arrange the two pieces in accordance with the respective multiple position data,
        project the two pieces onto the projection plane, and
        perform position adjustment processing of the two pieces using the projected two pieces.

2. The ultrasonic diagnostic apparatus according to claim 1, further comprising a position adjustment circuit configured to perform the position adjustment processing on the multiple 2D image data arranged in accordance with the respective multiple position data and to calculate multiple position correction data, wherein
    the correction circuit is configured to correct the multiple position data associated with the multiple 2D image data using corresponding position correction data of the multiple position correction data.

3. The ultrasonic diagnostic apparatus according to claim 1, wherein
    the associating circuit is configured to attach each of the multiple position data to each of the multiple 2D image data so as to associate each of the multiple position data with each of the multiple 2D image data.

4. The ultrasonic diagnostic apparatus according to claim 1, further comprising:

a volume generation circuit configured to generate volume data by arranging the multiple 2D image data based on the position data corrected by the correction circuit; and a 3D image generation circuit configured to generate 3D image data based on the volume data.

5. The ultrasonic diagnostic apparatus according to claim 1, wherein
the correction circuit is configured to set one or more ROIs (Regions of Interest) in the two pieces of 2D image data, and to perform the position adjustment processing based on the data in the ROIs.

6. The ultrasonic diagnostic apparatus according to claim 1, further comprising the ultrasonic probe including a 1D array including multiple oscillators one-dimensionally arranged.

7. The ultrasonic diagnostic apparatus according to claim 1, further comprising the ultrasonic probe including a 1D array including multiple oscillators one-dimensionally arranged, the 1D array being caused to mechanically oscillate.

8. The ultrasonic diagnostic apparatus according to claim 1, further comprising the ultrasonic probe including a 2D array including multiple oscillators two-dimensionally arranged.

9. The ultrasonic diagnostic apparatus according to claim 1, further comprising an image processing circuit configured to perform image processing for converting a histogram of each of the multiple 2D image data, wherein
the correction circuit is configured to correct the position data based on the multiple 2D image data subjected to the image processing.

10. The ultrasonic diagnostic apparatus according to claim 9, wherein
the image processing circuit is configured to enlarge a width of a pixel value in which a frequency of the histogram is present, or to convert the histogram into a designated distribution.

11. The ultrasonic diagnostic apparatus according to claim 1, further comprising an image processing circuit configured to perform image processing for reducing a speckle on the multiple 2D image data, wherein
the correction circuit is configured to correct the position data based on the multiple 2D image data subjected to the image processing.

12. The ultrasonic diagnostic apparatus according to claim 1, further comprising an image processing circuit configured to perform image processing for emphasizing a structure on the multiple 2D image data, wherein
the correction circuit is configured to correct the position data based on the multiple 2D image data subjected to the image processing.

13. The ultrasonic diagnostic apparatus according to claim 11, wherein
the image processing circuit is configured to perform, as the image processing, non-linear anisotropic diffusion filter processing, multiresolution decomposition/composition processing, high-frequency component control processing, or a combination thereof.

14. The ultrasonic diagnostic apparatus according to claim 1, wherein each of the multiple 2D image data is B-mode image data.

15. The ultrasonic diagnostic apparatus according to claim 1, further comprising a switch configured to switch whether or not to correct the position data.

16. The ultrasonic diagnostic apparatus according to claim 1, wherein
a part or whole of processing by the correction circuit is performed in parallel with processing by each of the transmitting and receiving circuit, the generation circuit, the acquisition circuit, and the associating circuit.

17. The ultrasonic diagnostic apparatus according to claim 1, wherein the correction circuit is configured to correct the position data and to perform a distortion correction for the multiple 2D image data.

18. The ultrasonic diagnostic apparatus according to claim 17, wherein the correction circuit is configured to use a linear conversion as the distortion correction for the multiple 2D image data.

19. The ultrasonic diagnostic apparatus according to claim 17, wherein the correction circuit is configured to use a distortion correction vector as the distortion correction for the multiple 2D image data.

20. The ultrasonic diagnostic apparatus according to claim 17, wherein the correction circuit is configured to use an image mosaicing as the distortion correction for the multiple 2D image data.

21. The ultrasonic diagnostic apparatus according to claim 1, wherein the acquisition circuit is configured to acquire the three-dimensional position data from a sensor attached to the ultrasonic probe.

22. A medical image processing apparatus that processes multiple 2D image data associated with respective three-dimensional multiple position data based on transmission and reception of an ultrasonic wave, the apparatus comprising:
a correction circuit configured to correct the multiple position data associated with the respective multiple 2D image data by performing position adjustment processing on the multiple 2D image data arranged in accordance with the respective multiple position data, wherein the correction circuit is configured to
set a projection plane between two pieces of the multiple 2D image data,
arrange the two pieces in accordance with the respective multiple position data,
project the two pieces onto the projection plane, and
perform position adjustment processing of the two pieces using the projected two pieces.

23. The ultrasonic diagnostic apparatus according to claim 1, wherein
the correction circuit is configured to select the two pieces as a reference piece and a piece to be corrected from the multiple 2D image data, the reference piece corresponding to corrected position data, and the piece to be corrected corresponding to non-corrected position data.

* * * * *